US009339395B2

(12) United States Patent
Prado et al.

(10) Patent No.: US 9,339,395 B2
(45) Date of Patent: May 17, 2016

(54) LOCK AND RELEASE IMPLANT DELIVERY SYSTEM

(71) Applicant: Xenco Medical LLC, San Diego, CA (US)

(72) Inventors: Gustavo R. Prado, San Diego, CA (US); Jason Haider, San Diego, CA (US)

(73) Assignee: XENCO MEDICAL, LLC, San Diego, CA (US)

( * ) Notice: Subject to any disclaimer, the term of this patent is extended or adjusted under 35 U.S.C. 154(b) by 0 days.

(21) Appl. No.: 14/553,748

(22) Filed: Nov. 25, 2014

(65) Prior Publication Data

US 2015/0157469 A1 Jun. 11, 2015

Related U.S. Application Data

(60) Provisional application No. 61/908,733, filed on Nov. 26, 2013.

(51) Int. Cl.
*A61F 2/46* (2006.01)
*A61F 2/44* (2006.01)
*A61F 2/30* (2006.01)

(52) U.S. Cl.
CPC .............. *A61F 2/4611* (2013.01); *A61F 2/447* (2013.01); *A61F 2/4455* (2013.01); *A61F 2/4601* (2013.01); *A61F 2002/308* (2013.01); *A61F 2002/30172* (2013.01); *A61F 2002/30228* (2013.01); *A61F 2002/30261* (2013.01); *A61F 2002/30772* (2013.01);
(Continued)

(58) Field of Classification Search
CPC ........... A61F 2/4611; A61F 2002/4627; A61F 2/4465
USPC ............................................................ 606/99
See application file for complete search history.

(56) References Cited

U.S. PATENT DOCUMENTS 2,397,216 A * 3/1946 Stellin ................. F16B 23/0007
411/404
6,503,279 B1 * 1/2003 Webb et al. ................ 623/17.16
(Continued)

FOREIGN PATENT DOCUMENTS

DE 202008011611 11/2008
EP 0716840 A2 6/1996
(Continued)

OTHER PUBLICATIONS

PCT/US2014/067506 ISR and Written Opinion dated Feb. 27, 2015.

*Primary Examiner* — Jan Christopher Merene
(74) *Attorney, Agent, or Firm* — Wilson Sonsini Goodrich & Rosati

(57) ABSTRACT

Injection-molded devices and systems for graft or other tissue delivery, methods for their single-use in delivery of an implant, and kits for their sterile delivery to a practitioner are disclosed herein. Systems for implant delivery comprise an injection moldable implant body and an insertion device comprising: an inner and outer shaft that form a locking mechanism that secures an implant body in place and releases it upon placement within a patient. Systems are configured to be manufactured by injection molding, such that they can be cost-effectively manufactured and discarded after a single use to avoid costs and risks associated with re-sterilization and cleaning, but can in some cases optionally also be manufactured by machining to be re-sterilized and reused.

25 Claims, 17 Drawing Sheets

(52) U.S. Cl.
CPC ............... *A61F 2002/30805* (2013.01); *A61F 2002/30808* (2013.01); *A61F 2002/30904* (2013.01); *A61F 2002/4475* (2013.01); *A61F 2002/4623* (2013.01); *A61F 2002/4627* (2013.01); *A61F 2002/4635* (2013.01)

(56) References Cited

U.S. PATENT DOCUMENTS

| | | | |
|---|---|---|---|
| 6,730,127 B2* | 5/2004 | Michelson | 623/17.16 |
| 6,767,366 B2* | 7/2004 | Lee et al. | 623/17.16 |
| 6,948,408 B1* | 9/2005 | Lee | B25B 15/008 81/436 |
| 8,216,316 B2* | 7/2012 | Kirschman | 623/17.16 |
| 8,465,546 B2 | 6/2013 | Jodaitis et al. | |
| 8,603,099 B2* | 12/2013 | Wright | A61F 2/4637 606/86 R |
| 8,685,100 B2 | 4/2014 | Jodaitis et al. | |
| 8,858,635 B2 | 10/2014 | Hovorka et al. | |
| 2003/0114931 A1 | 6/2003 | Lee | |
| 2003/0125739 A1* | 7/2003 | Bagga et al. | 606/61 |
| 2005/0096745 A1 | 5/2005 | Andre | |
| 2007/0100452 A1* | 5/2007 | Prosser | 623/17.11 |
| 2007/0118220 A1* | 5/2007 | Liu et al. | 623/17.11 |
| 2007/0168040 A1* | 7/2007 | Raymond | 623/17.15 |
| 2007/0282441 A1* | 12/2007 | Stream et al. | 623/17.11 |
| 2008/0221695 A1* | 9/2008 | Jacofsky et al. | 623/17.16 |
| 2009/0112220 A1 | 4/2009 | Kraus | |
| 2009/0281550 A1* | 11/2009 | Keller | A61F 2/4609 606/99 |
| 2010/0114105 A1* | 5/2010 | Butters | A61F 2/4611 606/99 |
| 2011/0106261 A1* | 5/2011 | Chin et al. | 623/17.16 |
| 2011/0112587 A1* | 5/2011 | Patel et al. | 606/86 A |
| 2011/0264218 A1 | 10/2011 | Assad | |
| 2012/0209383 A1 | 8/2012 | Tsuang | |
| 2013/0012999 A1 | 1/2013 | Petit | |
| 2013/0018382 A1 | 1/2013 | Jones | |

FOREIGN PATENT DOCUMENTS

| | | |
|---|---|---|
| WO | WO 2011/080426 | 7/2011 |
| WO | WO 2015/081142 | 6/2015 |

* cited by examiner

LOCK AND RELEASE IMPLANT DELIVERY SYSTEM

This application claims priority to U.S. Provisional Patent Application Ser. No. 61/908,733, filed Nov. 26, 2013, which is explicitly incorporated herein by reference in its entirety.

BACKGROUND OF THE INVENTION

Traditionally, implant insertion device and spinal implant are machined individually to accommodate the need of different patient and different surgical procedures.

SUMMARY OF THE INVENTION

Machinable implant insertion devices and implants can be individually tailored to the needs of the patient, practitioner and/or the medical procedure. However, the cost of machining each implant insertion device and implant with different materials and sizes is significantly higher than molding an injection moldable equivalent. The cost of these reusable devices and implants is manifest in their manufacture but also in the expense of professional device cleaning, autoclaving, sterilization, transport, and maintenance. The risk of contamination rises with the complex procedure for cleaning and transporting the devices and implants between usages. There are also costs and risks associated with dealing with infections caused by failure to clean and sterilize.

Injection moldable implant insertion devices and implant bodies can be molded using one or more durable materials at a lower price than their machinable equivalents. In addition, the injection moldable implant insertion devices and implant bodies are easily made and can be deployed for single use only, so that the contamination associated with the cleaning, autoclaving, sterilization, transportation, or maintenance of the machined equivalents are significantly reduced or completely eliminated. Thus, the cost of the implant insertion device and implant body per usage is significantly lower than the re-usable machined equivalent, even if the devices are discarded after a single use. Further, injection moldable implant insertion devices and implants can be packed in sterile and peelably sealed kits to prevent contamination and facilitate surgical needs in different medical procedures.

In some aspects, disclosed herein are implant delivery systems comprising: an implant body comprising a support structure and an internal space, the support structure comprising: an outer surface; a main slot indented into the outer surface; a chamber indented from the main slot, the chamber being deeper than the main slot; two side slots at the outer surface proximal to the main slot; wherein the implant body is substantially toroidal, the internal space is not covered at a top cross section and a bottom cross section thereof by the support structure, and the internal space is configured to receive at least one graft material therewithin; and an implant insertion device comprising: an inner shaft comprising: an inner shaft body; a knob at a base of the inner shaft body, the knob comprising a cam feature; an inner shaft tip at an insertion end of the inner shaft body, wherein the inner shaft tip is not substantially cylindrically circular and the inner shaft tip is wider than the inner shaft body immediately adjacent thereto in at least one dimension perpendicular to a plane of rotation of the inner shaft tip; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft, the outer shaft opening being configured to allow passage of the inner shaft tip; two outer shaft tips at the outer face to fit the two side slots of the implant body; a first surface at a base of the outer shaft configured to receive the cam feature of the knob at a first position; a second surface at the base of the outer shaft configured to receive the cam feature of the knob at a second position; a stopper at the base of the outer shaft configured to stop the cam feature at the first or the second position; a ramp at the base of the outer shaft, wherein the ramp connects the first surface to the second surface, wherein the inner shaft is configured to rotate within the outer shaft such that the cam feature moves to the first position or the second position at the base of the outer shaft, wherein the rotation of the inner shaft is configured to transform into a linear movement of the inner shaft along a direction perpendicular to a plane of the rotation of the inner shaft tip, wherein the inner shaft tip is configured to fit through the main slot of the implant body and rotate in the chamber of the implant body so as to lock or unlock the implant body to the inner shaft, and the two side slots of the implant body are configured to fit the two outer shaft tips at the outer face of the outer shaft so as to attach the implant body to the outer shaft, and wherein the inner shaft is unlocked from the outer shaft at the first position and the inner shaft is locked to the outer shaft at the second position.

In some aspects, disclosed herein are implant delivery systems comprising: an implant insertion device comprising: an inner shaft comprising: an inner shaft body; a knob at a base of the inner shaft body, the knob comprising a first interface; an inner shaft tip at an insertion end of the inner shaft body, wherein the inner shaft tip is not substantially cylindrically circular; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft; a first complementary interface at a base of the outer shaft configured to receive the first interface of the inner shaft; a second complementary interface at the outer face to receive a second interface of the implant body; wherein a rotation of the inner shaft is configured to associate the first complementary interface to the first interface at a first position or at a second position, wherein the inner shaft tip is configured to fit through a main slot of an implant body and rotate in a chamber of the implant body so as to lock the implant body to the inner shaft.

In some cases, disclosed herein are implant delivery systems comprising: an implant insertion device comprising: an inner shaft comprising: an inner shaft body; a knob at a base of the inner shaft body, the knob comprising a first interface; an inner shaft tip at an insertion end of the inner shaft body, wherein the inner shaft tip is not substantially cylindrically circular; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft; a first complementary interface at a base of the outer shaft configured to receive the first interface of the knob; a second complementary interface at the outer face; an implant body comprising a support structure and an internal space, the support structure comprising: an outer surface; a main slot indented into the outer surface; a chamber indented from the main slot and deeper than the main slot; a second interface at the outer surface proximal to the main slot to fit the second complimentary interface at the outer face; wherein the implant body is substantially toroidal, the internal space is not covered at a top cross section, a bottom cross section, or the top and the bottom cross sections thereof by the support structure, and the internal space is configured to receive at least one graft material, wherein a rotation of the inner shaft is configured to associate the first complementary interface to the first interface at a first position or a second position, wherein the inner shaft tip is configured to fit through a main slot of an implant body and rotate in a chamber of the implant body so as to lock the implant body to the inner shaft.

In some aspects, disclosed herein are methods for delivering an implant body using an implant insertion device comprising: locking the implant body to the implant insertion device by rotating a knob of an inner shaft of the implant insertion device in a manner such that the rotation of the knob: rotates an inner shaft tip within a chamber of the implant body such that a major axis of a main slot and a major axis of the inner shaft tip are not substantially parallel, linearly moves the implant body towards an insertion end of an outer shaft of the implant insertion device so as to secure the implant body against the insertion end of the outer shaft, delivering the implant body into a subject using the implanting insertion device; reversely rotating the knob of the inner shaft of the implant insertion device in a manner such that the reverse rotation of the knob rotates the inner shaft tip within the main slot in the implant body such that the major axis of the main slot and the major axis of the inner shaft tip are substantially parallel, associates the first interface of the knob to the first complimentary interface at the outer shaft at a second position. In some aspects the methods comprise inserting the implant into an intervertebral space. In some aspects the intervertebral space is lumbar. In some aspects the intervertebral space is cervical. In some aspects intervertebral disk material is removed from the intervertebral space prior to inserting the implant. In some aspects the implant is inserted into the interior of an intervertebral disk.

In some cases, disclosed herein are methods for delivering an implant body using an implant insertion device comprising releasing an implant body into an intervertebral space of a patient comprising: rotating a knob of an inner shaft of the implant insertion device in a manner such that a rotation of the knob rotates an inner shaft tip within a main slot in the implant body substantially in a coronal plane such that a major axis of the main slot and a major axis of the inner shaft tip are substantially parallel, and associates a first interface of the knob to a first complimentary interface at an outer shaft at a unlocked position; and depositing the implant body in an intervertebral space of the patient. In some aspects the methods comprise inserting the implant into an intervertebral space. In some aspects the intervertebral space is lumbar. In some aspects the intervertebral space is cervical. In some aspects intervertebral disk material is removed from the intervertebral space prior to inserting the implant. In some aspects the implant is inserted into the interior of an intervertebral disk.

In some aspects, disclosed herein are sterile kits containing a single-use implant body insertion device and a single use implant, the sterile kit comprising: a sterile kit cover sealed to enclose at least one device tray, at least one implant body, and at least one implant insertion device therewithin, wherein the at least one implant body and the at least one implant insertion device are configured for a single usage; the at least one device tray is configured to secure: the at least one implant insertion device; the at least one implant body; the at least one implant insertion device comprising: a shaft; a tip; a first interface for locking the at least one implant body; a second interface for locking the at least one implant body; a first position; a second position; and the at least one implant body comprising: an internal space; a slot for locking the at least one implant body against the at least one implant insertion device at the first position; a first complimentary interface for receiving the interface of the at least one implant insertion device at the first position or the second position; a second complimentary interface for receiving the second interface of the at least one implant insertion device at the first position. In some aspects, sterile kits may also contain pre-assembled grafting material within the graft window of implant. Grafting material may be packed allograft bone (demineralized or not), packed biocompatible ceramics granules (beta-tricalcium phosphate, hydroxyapatite, calcium sulfate, and equivalents) to assume the graft volume shape, biocompatible ceramic granules held by biocompatible matrix such as collagen with or without bioglass and with or without hyaluronic acid.

DETAILED DESCRIPTION OF THE INVENTION

Figure 1A:
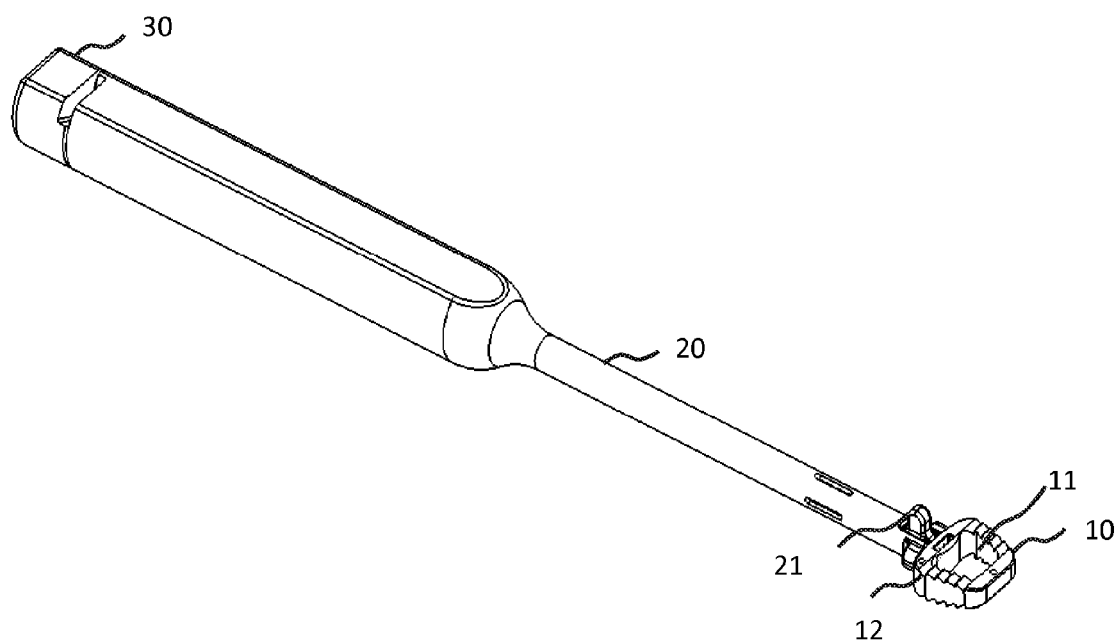
FIG. 1a shows an embodiment of the implant insertion device and the implant body attached to the implant insertion device.

Chronic spinal pain is a common issue among a large number of people worldwide, and is a major health and quality of life concern. Back pain can impair one's ability to work, concentrate and exercise, thus having a substantial effect on one's quality of life. Spinal pain, either in the neck or back, is often associated with damage to one or more intervertebral discs. A herniated disc may exude its soft, internal protective material (nucleus pulposus) outside of the disc area. When this exuded material presses on the nerves that run down the spine, the result can be a loss of range of motion, sharp localized pain, and/or dull radiating pain to one or more extremities. Secondary effects of spinal pain can include depression, loss of work efficiency, and early cognitive degeneration.

One effective approach to addressing spinal pain is fusion of the adjacent vertebrae. Fusion of adjacent vertebrae can be accomplished by introduction of graft tissue between the vertebrae, such as into the herniated disc or into a space created by removal of the herniated disc. Graft tissue, as used herein, may comprise autologous patient tissue, such as bone tissue taken from elsewhere in the patient during the procedure. Graft tissue may be cadaverous, or cultured or synthetically produced from differentiated or undifferentiated cell populations derived from the patient or elsewhere. Graft tissue, if properly inserted and protected, can lead to fusion of the adjacent vertebrae.

Stabilizing graft tissue is a major challenge. The spinal column, particularly the lumbar spine and the cervical spine, must sustain substantial pressures, and these pressures can easily disrupt an unstabilized graft. The graft material must be delivered into the intervertebral space with a minimum of damage to the surrounding tissue.

In addition, contamination or infection of the graft material or the insertion site during the procedure is a major risk. Current methods and devices for insertion of graft material involve reusable, machined materials that must be sterilized between uses. Although this process allows re-use of the devices, the sterilization process is costly and not without risk, as unsuccessfully sterilized or unclean materials can lead to major complications.

Injection-molded devices can be made out of materials that are substantially less costly to produce, without loss in single-use material durability. These injection molded devices can be sterilely manufactured and packaged, so that they can be delivered to an operating room without risk of contamination. Once used, they are disposed of rather than being cleaned and sterilized. This single-use aspect has both medical and economic benefits: the risk of infection is greatly reduced relative to the risk associated with multi-use devices; and the cost of manufacturing injection-molded devices is substantially lower than the cost of sterilizing devices for re-use.

Accordingly, the single-use, injection moldable devices and methods disclosed herein are able to increase patient health, reduce risk of infection and reduce health costs.

Disclosed herein, in certain embodiments, are implant delivery systems comprising: an implant body comprising a support structure and an internal space, the support structure comprising: an outer surface; a main slot indented into the outer surface; a chamber indented from the main slot, the chamber being deeper than the main slot; two side slots at the outer surface proximal to the main slot; wherein the implant body is substantially toroidal, the internal space is not covered at a top cross section and a bottom cross section thereof by the support structure, and the internal space is configured to receive at least one graft material therewithin; and an implant insertion device comprising: an inner shaft comprising: an inner shaft body; a knob at a base of the inner shaft body, the knob comprising a cam feature; an inner shaft tip at an insertion end of the inner shaft body, wherein the inner shaft tip is not substantially cylindrically circular and the inner shaft tip is wider than the inner shaft body immediately adjacent thereto in at least one dimension perpendicular to a plane of rotation of the inner shaft tip; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft, the outer shaft opening being configured to allow passage of the inner shaft tip; two outer shaft tips at the outer face to fit the two side slots of the implant body; a first surface at a base of the outer shaft configured to receive the cam feature of the knob at a first position; a second surface at the base of the outer shaft configured to receive the cam feature of the knob at a second position; a stopper at the base of the outer shaft configured to stop the cam feature at the first or the second position; a ramp at the base of the outer shaft, wherein the ramp connects the first surface to the second surface, wherein the inner shaft is configured to rotate within the outer shaft such that the cam feature moves to the first position or the second position at the base of the outer shaft, wherein the rotation of the inner shaft is configured to transform into a linear movement of the inner shaft along a direction perpendicular to a plane of the rotation of the inner shaft tip, wherein the inner shaft tip is configured to fit through the main slot of the implant body and rotate in the chamber of the implant body so as to lock or unlock the implant body to the inner shaft, and the two side slots of the implant body are configured to fit the two outer shaft tips at the outer face of the outer shaft so as to attach the implant body to the outer shaft, and wherein the inner shaft is unlocked from the outer shaft at the first position and the inner shaft is locked to the outer shaft at the second position.

Also disclosed herein, in certain embodiments, are implant delivery systems comprising: an implant insertion device comprising: an inner shaft comprising: an inner shaft body; a knob at a base of the inner shaft body, the knob comprising a first interface; an inner shaft tip at an insertion end of the inner shaft body, wherein the inner shaft tip is not substantially cylindrically circular; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft; a first complementary interface at a base of the outer shaft configured to receive the first interface of the inner shaft; a second complementary interface at the outer face to receive a second interface of the implant body; wherein a rotation of the inner shaft is configured to associate the first complementary interface to the first interface at a first position or at a second position, wherein the inner shaft tip is configured to fit through a main slot of an implant body and rotate in a chamber of the implant body so as to lock the implant body to the inner shaft. In some cases, the implant delivery system comprises an implant body comprising a support structure and an internal space, the support structure comprising: an outer surface; a main slot indented into the outer surface; a chamber indented from the main slot, the chamber being deeper than the main slot; the second interface at the outer surface proximal to the main slot; wherein the implant body is substantially toroidal, and the internal space is not covered at a top cross section, a bottom cross section, or the top and bottom cross sections thereof by the support structure, and the internal space is configured to receive at least one graft material; and an internal space configured to contain at least a graft material. In some cases, the second interface of the implant body is configured to fit the second complementary interface at the outer face of the outer shaft so as to attach the implant body to the outer shaft. In some cases, the implant insertion device is disposable. In some cases, the implant insertion device is for one-time use only. In some cases, the implant insertion device is injection moldable. In some cases, the implant delivery system is disposable. In some cases, the implant delivery system is for one-time use only. In some cases, the second interface comprises at least one side slot indented into the implant body proximal to the main slot, wherein each side slot is configured to receive an outer shaft tip. In some cases, the at least one side slot is peripherally proximal to the main slot. In some cases, the at least one side slot is shallower than the main slot. In some cases, the main slot and the at least one side slot are indented into the supporting structure. In some cases, wherein the main slot is indented deeper into the wall of the implant body than the two side slots along the insertion direction. In some cases, the internal space of the implant body is filled at least partly by at least one graft material. In some cases, the implant body is substantially toroidal. In some cases, wherein a toroidal shape is a shape with a plurality of cross sections stacked together continuously, each cross section having an arbitrary two dimensional empty area enclosed by a wall. In some cases, the height of the implant body is non-uniform along the anterior-to-posterior direction so as to accommodate the lordosis angle of the spinal cord when the implant body is properly inserted. In some cases, a toroidal shape is a shape comprising a hole throughout an arbitrary three dimensional volume. In some cases, the internal space is not covered at the top cross section, bottom cross section, or top and bottom cross sections thereof by the implant body. In some cases, the implant body enclosing the internal space has a wall thickness of at least 1 millimeter but no more than 3 centimeters. In some cases, the implant body comprises at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the implant body is injection moldable. In some cases, the implant body is machinable. In some cases, the implant body comprises a saw tooth configured to allow unidirectional insertion into a subject on an outer surface of the implant body. In some cases, the saw tooth is further located on the longitudinal plane of the implant body. In some cases, the saw tooth is configured to prevent sliding back-out of an implant body after an insertion. In some cases, the implant body comprises at least one space for accommodating at least one detectable tag. In some cases, the at least one detectable tag comprise a radio frequency detectable tag. In some cases, the at least one space are in the wall of the implant body. In some cases, the implant body comprises two spaces for detectable tags, the two spaces being not greater than 5 mm in their widest dimension. In some cases, the implant body comprises two spaces for detectable tags, the two spaces being spatially separated from each other. In some cases, the implant body comprises four spaces for detectable tags, the four spaces being spatially separated from each other. In some cases, the cross section of the implant body along a longitudinal plane comprises a closed contour formed by the implant body. In some cases, wherein the closed contour encloses an area therewithin. In some cases, the internal space is enclosed by closed contours in a plurality of adjacent longitudinal planes. In some cases, the cross section of the implant body along a longitudinal plane is a square, a rectangle, a circle, an ellipse, a rhombus, a trapezoid, a pentagon, or an arbitrary two dimensional shape enclosing an empty two dimensional area in a closed contour by a wall. In some cases, the cross section of the implant body along a longitudinal plane is a two-dimensional shape similar to a cross section of the intervertebral space to be inserted therein. In some cases, the cross section of the implant body along a longitudinal plane is comprises a closed contour with a non-uniform thickness along the closed contour. In some cases, the non-uniform thickness along the closed contour is filled with at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the chamber of the implant body is connected to a slot indented from a top-most region or a bottom-most region of the outer surface along the longitudinal direction. In some cases, wherein the slot at the top-most region or the bottom-most region of the support structure is configured to facilitate injection molding of the chamber. In some cases, the slot at the top-most region or the bottom-most of the support structure is configured to enable visualization of the inner shaft tip. In some cases, the inner shaft is disposable. In some cases, the inner shaft is for one-time use only. In some cases, the inner shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the inner shaft comprises about 50% glass. In some cases, the inner shaft comprises a glass content of at least 10% to no greater than 70%. In some cases, the inner shaft tip comprises at least one metal. In some cases, the inner shaft body comprises at least one metal. In some cases, the inner shaft is injection moldable. In some cases, the inner shaft tip is injection moldable. In some cases, the inner shaft body is injection moldable. In some cases, the knob is injection moldable. In some cases, the inner shaft is injection moldable and machinable. In some cases, the inner shaft body is substantially cylindrical. In some cases, the inner shaft body is flexible so as to fit in a curved outer shaft body. In some cases, the inner shaft body is a cylinder. In some cases, the knob of the inner shaft is not enclosed in the outer shaft. In some cases, the inner shaft tip is not enclosed in the outer shaft. In some cases, the inner shaft tip is connected to the inner shaft body in a manner such that the inner shaft tip rotates concentrically when the inner shaft body rotates. In some cases, the inner shaft tip is attached to the inner shaft body such that the center of the cross section of the inner shaft body overlaps with the middle point of the two foci of the inner shaft tip. In some cases, the linear movement draws the inner shaft tip towards the two outer shaft tips. In some cases, the inner shaft tip is substantially rectangular cuboid or cylindrically elliptical. In some cases, the inner shaft comprises at least two protrusions proximal to the inner shaft tip. In some cases, the at least two protrusions are configured to ensure concentric rotation of the inner shaft within the outer shaft. In some cases, the at least two protrusions contact an inner surface of the outer shaft. In some cases, the first or the second interface comprises a camping some cases, the cam feature is semi-circular. In some cases, the cam feature is substantially a circle sector, a triangle, a quadrilateral, or a pentagon. In some cases, the cam feature is substantially a circle sector with a central angle of at least 15 degrees to up to 275 degrees. In some cases, the cam feature is substantially a triangle, a quadrilateral, or a pentagon with an angle of at least 15 degrees to up to 150 degrees. In some cases, the cam feature is attached to the knob of the inner shaft. In some cases, the knob is substantially cylindrical. In some cases, the cross section of the knob is greater than the cross section of the inner shaft body. In some cases, the knob of the inner shaft is configured to not fit into the outer shaft at the base of the outer shaft. In some cases, the knob comprises at least one hump. In some cases, the hump is configured to lock the inner shaft to the outer shaft at the second position such that the inner shaft does not rotate with respect to the outer shaft. In some cases, the inner shaft tip is substantially rectangular cuboid or cylindrically elliptical. In some cases, the inner shaft tip is configured to fit and rotate in the chamber of the implant body. In some cases, the inner shaft tip is configured to pass through the outer shaft opening. In some cases, the inner shaft tip is configured to pass through the outer shaft opening only when a major axis of the inner shaft tip and a major axis of the outer shaft opening are substantially parallel. In some cases, the first or the second complimentary interface comprises a cam feature. In some cases, the first or the second interface comprises a first surface and a second surface, wherein the first surface and the second surface are connected by a ramp. In some cases, the first and the second surface are displaced by a distance that the inner shaft tip is capable of moving with respect to the outer shaft. In some cases, the first and the second surface are displaced by a distance, the distance determined by a length and a rising angle of the ramp. In some cases, the first or the second interface comprises at least one slot. In some cases, the first or the second complimentary interface comprises at least a slot. In some cases, the first or the second interface comprises at least one tip. In some cases, the outer shaft body is curved. In some cases, the outer shaft is disposable. In some cases, the outer shaft is for one-time use only. In some cases, the outer shaft comprises at least one material selected from the list consists of carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the outer shaft comprises about 50% glass. In some cases, the outer shaft comprises a material having a glass content of at least 10% to no greater than 70%. In some cases, the outer shaft is injection moldable. In some cases, the outer shaft is injection moldable and machinable. In some cases, the cross sectional area of the outer shaft is monotonically non-increasing from a base of the outer shaft to an insertion end of the outer shaft. In some cases, the outer shaft opening is substantially circular. In some cases, the outer shaft opening is configured to allow passage of the inner shaft tip. In some cases, the outer shaft comprises a third interface, wherein the third interface unlocks to the hump at the first position and locks to the hump at the second position. In some cases, the outer shaft comprises at least one insertion stopper on the outer shaft to limit insertion depth into an intervertebral space of the subject. In some cases, the outer shaft comprises at least an insertion stopper attached to the outer shaft. In some cases, the outer shaft comprises at least an insertion stopper, the height of the insertion stopper being greater than 0.2 millimeters but less than 2 centimeters. In some cases, the outer shaft comprises at least a ramped protrusion to prevent the inner shaft from sliding out while the inner shaft is inserted therewithin. In some cases, the outer shaft comprises at least a ramped protrusion so that the inner shaft only comes out of the outer shaft when the implant body is not locked to an inner shaft tip. In some cases, the outer shaft comprises at least a ramped protrusion so that the inner shaft only comes out of the outer shaft when the major axis of the inner shaft tip and the major axis of the main slot of the implant body are substantially perpendicular. In some cases, the outer shaft opening at the insertion end of the outer shaft is further configured to allow passage of the inner shaft tip only when the major axis of the inner shaft tip and the major axis of the outer shaft opening are substantially parallel. In some cases, the first complimentary interface comprises a first surface and a second surface. In some cases, the first surface and the second surface are semi-circular. In some cases, the first surface and the second surface are a portion of a circle sector. In some cases, the first surface and the second surface are a portion of a circle sector with a central angle of 45, 60, 90, 120, or 150 degrees. In some cases, the first surface and the second surface are a portion of a circle sector with a central angle of at least 15 degrees to up to 275 degrees. In some cases, the first surface and the second surface are a portion of a circle sector with a central angle of 65, 75, 85, 90, 95, 105, or 115 degrees. In some cases, the first or the second complimentary interface comprises at least one tip. In some cases, the at least one tip is substantially semi-rectangular cuboid or semi-cylindrically elliptical. In some cases, the at least one tip is peripherally proximal to the outer shaft opening at the insertion end of the outer shaft. In some cases, the at least one tip and another tip are symmetrically adjacent to the outer shaft opening at the insertion end of the outer shaft, and on an extension of the major axis of the outer shaft opening. In some cases, the at least one tip is on the outer face of the outer shaft. In some cases, each tip is substantially semi-rectangular cuboid or semi-cylindrically elliptical. In some cases, each tip is configured to fit in one side slot of the implant body when the implant body is locked to the outer shaft. In some cases, the locking the implant body to the inner shaft comprises that a major axis of the main slot and a major axis of the inner shaft tip are not substantially parallel. In some cases, not substantially parallel comprises an angle of about 90 degrees between the major axis of the main slot and a major axis of the inner shaft tip. In some cases, the linear movement of the inner shaft body is determined by a height of the interface or the complimentary interface and a rotation angle that the cam feature rotates from a predetermined location along a circumference of the knob.

Also disclosed herein, in certain embodiments, are implant delivery systems comprising: an implant insertion device comprising: an inner shaft comprising: an inner shaft body; a knob at a base of the inner shaft body, the knob comprising a first interface; an inner shaft tip at an insertion end of the inner shaft body, wherein the inner shaft tip is not substantially cylindrically circular; an outer shaft configured to hold the inner shaft body therein, the outer shaft comprising: a hollow outer shaft body, wherein the outer shaft body is configured to accommodate the inner shaft body therewithin; an outer face; an outer shaft opening at the outer face of the outer shaft; a first complementary interface at a base of the outer shaft configured to receive the first interface of the knob; a second complementary interface at the outer face; an implant body comprising a support structure and an internal space, the support structure comprising: an outer surface; a main slot indented into the outer surface; a chamber indented from the main slot and deeper than the main slot; a second interface at the outer surface proximal to the main slot to fit the second complementary interface at the outer face; wherein the implant body is substantially toroidal, the internal space is not covered at a top cross section, a bottom cross section, or the top and the bottom cross sections thereof by the support structure, and the internal space is configured to receive at least one graft material, wherein a rotation of the inner shaft is configured to associate the first complementary interface to the first interface at a first position or a second position, wherein the inner shaft tip is configured to fit through a main slot of an implant body and rotate in a chamber of the implant body so as to lock the implant body to the inner shaft. In some cases, the implant delivery system comprises an implant body comprising a support structure and an internal space, the support structure comprising: an outer surface; a main slot indented into the outer surface; a chamber indented from the main slot, the chamber being deeper than the main slot; the second interface at the outer surface proximal to the main slot; wherein the implant body is substantially toroidal, and the internal space is not covered at a top cross section, a bottom cross section, or the top and bottom cross sections thereof by the support structure, and the internal space is configured to receive at least one graft material; and an internal space configured to contain at least a graft material. In some cases, the second interface of the implant body is configured to fit the second complementary interface at the outer face of the outer shaft so as to attach the implant body to the outer shaft. In some cases, the implant insertion device is disposable. In some cases, the implant insertion device is for one-time use only. In some cases, the implant insertion device is injection moldable. In some cases, the implant delivery system is disposable. In some cases, implant delivery system for one-time use only. In some cases, the second interface comprises at least one side slot indented into the implant body proximal to the main slot, wherein each side slot is configured to receive an outer shaft tip. In some cases, the at least one side slot is peripherally proximal to the main slot. In some cases, the at least one side slot is shallower than the main slot. In some cases, the main slot and the at least one side slot are indented into the supporting structure. In some cases, wherein the main slot is indented deeper into the wall of the implant body than the two side slots along the insertion direction. In some cases, the internal space of the implant body is filled at least partly by at least one graft material. In some cases, the implant body is substantially toroidal. In some cases, wherein a toroidal shape is a shape with a plurality of cross sections stacked together continuously, each cross section having an arbitrary two dimensional empty area enclosed by a wall. In some cases, the height of the implant body is non-uniform along the anterior-to-posterior direction so as to accommodate the lordosis angle of the spinal cord when the implant body is properly inserted. In some cases, a toroidal shape is a shape comprising a hole throughout an arbitrary three dimensional volume. In some cases, the internal space is not covered at the top cross section, bottom cross section, or top and bottom cross sections thereof by the implant body. In some cases, the implant body enclosing the internal space has a wall thickness of at least 1 millimeter but no more than 3 centimeters. In some cases, the implant body comprises at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the implant body is injection moldable. In some cases, the implant body is machinable. In some cases, the implant body comprises a saw tooth configured to allow unidirectional insertion into a subject on an outer surface of the implant body. In some cases, the saw tooth is further located on the longitudinal plane of the implant body. In some cases, the saw tooth is configured to prevent sliding back-out of an implant body after an insertion. In some cases, the implant body comprises at least one space for accommodating at least one detectable tag. In some cases, the at least one detectable tag comprise a radio frequency detectable tag. In some cases, the at least one space are in the wall of the implant body. In some cases, the implant body comprises two spaces for detectable tags, the two spaces being not greater than 5 mm in their widest dimension. In some cases, the implant body comprises two spaces for detectable tags, the two spaces being spatially separated from each other. In some cases, the implant body comprises four spaces for detectable tags, the four spaces being spatially separated from each other. In some cases, the cross section of the implant body along a longitudinal plane comprises a closed contour formed by the implant body. In some cases, wherein the closed contour encloses an area therewithin. In some cases, the internal space is enclosed by closed contours in a plurality of adjacent longitudinal planes. In some cases, the cross section of the implant body along a longitudinal plane is a square, a rectangle, a circle, an ellipse, a rhombus, a trapezoid, a pentagon, or an arbitrary two dimensional shape enclosing an empty two dimensional area in a closed contour by a wall. In some cases, the cross section of the implant body along a longitudinal plane is a two-dimensional shape similar to a cross section of the intervertebral space to be inserted therein. In some cases, the cross section of the implant body along a longitudinal plane comprises a closed contour with a non-uniform thickness along the closed contour. In some cases, the non-uniform thickness along the closed contour is filled with at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the chamber of the implant body is connected to a slot indented from a top-most region or a bottom-most region of the outer surface along the longitudinal direction. In some cases, wherein the slot at the top-most region or the bottom-most region of the support structure is configured to facilitate injection molding of the chamber. In some cases, the slot at the top-most region or the bottom-most of the support structure is configured to enable visualization of the inner shaft tip. In some cases, the inner shaft is disposable. In some cases, the inner shaft is for one-time use only. In some cases, the inner shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the inner shaft comprises about 50% glass. In some cases, the inner shaft comprises a glass content of at least 10% to no greater than 70%. In some cases, the inner shaft tip comprises at least one metal. In some cases, the inner shaft body comprises at least one metal. In some cases, the inner shaft is injection moldable. In some cases, the inner shaft tip is injection moldable. In some cases, the inner shaft body is injection moldable. In some cases, the knob is injection moldable. In some cases, the inner shaft is injection moldable and machinable. In some cases, the inner shaft body is substantially cylindrical. In some cases, the inner shaft body is flexible so as to fit in a curved outer shaft body. In some cases, the inner shaft body is a cylinder. In some cases, the knob of the inner shaft is not enclosed in the outer shaft. In some cases, the inner shaft tip is not enclosed in the outer shaft. In some cases, the inner shaft tip is connected to the inner shaft body in a manner such that the inner shaft tip rotates concentrically when the inner shaft body rotates. In some cases, the inner shaft tip is attached to the inner shaft body such that the center of the cross section of the inner shaft body overlaps with the middle point of the two foci of the inner shaft tip. In some cases, the linear movement draws the inner shaft tip towards the two outer shaft tips. In some cases, the inner shaft tip is substantially rectangular cuboid or cylindrically elliptical. In some cases, the inner shaft comprises at least two protrusions proximal to the inner shaft tip. In some cases, the at least two protrusions are configured to ensure concentric rotation of the inner shaft within the outer shaft. In some cases, the at least two protrusions contact an inner surface of the outer shaft. In some cases, the first or the second interface comprises a camping some cases, the cam feature is semi-circular. In some cases, the cam feature is substantially a circle sector, a triangle, a quadrilateral, or a pentagon. In some cases, the cam feature is substantially a circle sector with a central angle of at least 15 degrees to up to 275 degrees. In some cases, the cam feature is substantially a triangle, a quadrilateral, or a pentagon with an angle of at least 15 degrees to up to 150 degrees. In some cases, the cam feature is attached to the knob of the inner shaft. In some cases, the knob is substantially cylindrical. In some cases, the cross section of the knob is greater than the cross section of the inner shaft body. In some cases, the knob of the inner shaft is configured to not fit into the outer shaft at the base of the outer shaft. In some cases, the knob comprises at least one hump. In some cases, the hump is configured to lock the inner shaft to the outer shaft at the second position such that the inner shaft does not rotate with respect to the outer shaft. In some cases, the inner shaft tip is substantially rectangular cuboid or cylindrically elliptical. In some cases, the inner shaft tip is configured to fit and rotate in the chamber of the implant body. In some cases, the inner shaft tip is configured to pass through the outer shaft opening. In some cases, the inner shaft tip is configured to pass through the outer shaft opening only when a major axis of the inner shaft tip and a major axis of the outer shaft opening are substantially parallel. In some cases, the first or the second complimentary interface comprises a cam feature. In some cases, the first or the second interface comprises a first surface and a second surface, wherein the first surface and the second surface are connected by a ramp. In some cases, the first and the second surface are displaced by a distance that the inner shaft tip is capable of moving with respect to the outer shaft. In some cases, the first and the second surface are displaced by a distance, the distance determined by a length and a rising angle of the ramp. In some cases, the first or the second interface comprises at least one slot. In some cases, the first or the second complimentary interface comprises at least a slot. In some cases, the first or the second interface comprises at least one tip. In some cases, the outer shaft body is curved. In some cases, the outer shaft is disposable. In some cases, the outer shaft is for one-time use only. In some cases, the outer shaft comprises at least one material selected from the list consists of carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the outer shaft comprises about 50% glass. In some cases, the outer shaft comprises a material having a glass content of at least 10% to no greater than 70%. In some cases, the outer shaft is injection moldable. In some cases, the outer shaft is injection moldable and machinable. In some cases, the cross sectional area of the outer shaft is monotonically non-increasing from a base of the outer shaft to an insertion end of the outer shaft. In some cases, the outer shaft opening is substantially circular. In some cases, the outer shaft opening is configured to allow passage of the inner shaft tip. In some cases, the outer shaft comprises a third interface, wherein the third interface unlocks to the hump at the first position and locks to the hump at the second position. In some cases, the outer shaft comprises at least one insertion stopper on the outer shaft to limit insertion depth into an intervertebral space of the subject. In some cases, the outer shaft comprises at least an insertion stopper attached to the outer shaft. In some cases, the outer shaft comprises at least an insertion stopper, the height of the insertion stopper being greater than 0.2 millimeters but less than 2 centimeters. In some cases, the outer shaft comprises at least a ramped protrusion to prevent the inner shaft from sliding out while the inner shaft is inserted therewithin. In some cases, the outer shaft comprises at least a ramped protrusion so that the inner shaft only comes out of the outer shaft when the implant body is not locked to an inner shaft tip. In some cases, the outer shaft comprises at least a ramped protrusion so that the inner shaft only comes out of the outer shaft when the major axis of the inner shaft tip and the major axis of the main slot of the implant body are substantially perpendicular. In some cases, the outer shaft opening at the insertion end of the outer shaft is further configured to allow passage of the inner shaft tip only when the major axis of the inner shaft tip and the major axis of the outer shaft opening are substantially parallel. In some cases, the first complimentary interface comprises a first surface and a second surface. In some cases, the first surface and the second surface are semi-circular. In some cases, the first surface and the second surface are a portion of a circle sector. In some cases, the first surface and the second surface are a portion of a circle sector with a central angle of 45, 60, 90, 120, or 150 degrees. In some cases, the first surface and the second surface are a portion of a circle sector with a central angle of at least 15 degrees to up to 275 degrees. In some cases, the first surface and the second surface are a portion of a circle sector with a central angle of 65, 75, 85, 90, 95, 105, or 115 degrees. In some cases, the first or the second complimentary interface comprises at least one tip. In some cases, the at least one tip is substantially semi-rectangular cuboid or semi-cylindrically elliptical. In some cases, the at least one tip is peripherally proximal to the outer shaft opening at the insertion end of the outer shaft. In some cases, the at least one tip and another tip are symmetrically adjacent to the outer shaft opening at the insertion end of the outer shaft, and on an extension of the major axis of the outer shaft opening. In some cases, the at least one tip is on the outer face of the outer shaft. In some cases, each tip is substantially semi-rectangular cuboid or semi-cylindrically elliptical. In some cases, each tip is configured to fit in one side slot of the implant body when the implant body is locked to the outer shaft. In some cases, the locking the implant body to the inner shaft comprises that a major axis of the main slot and a major axis of the inner shaft tip are not substantially parallel. In some cases, not substantially parallel comprises an angle of about 90 degrees between the major axis of the main slot and a major axis of the inner shaft tip. In some cases, the linear movement of the inner shaft body is determined by a height of the interface or the complimentary interface and a rotation angle that the cam feature rotates from a predetermined location along a circumference of the knob.

Also disclosed herein, in certain cases, are methods for delivering an implant body using an implant insertion device comprising: locking the implant body to the implant insertion device by rotating a knob of an inner shaft of the implant insertion device in a manner such that the rotation of the knob: rotates an inner shaft tip within a chamber of the implant body such that a major axis of a main slot and a major axis of the inner shaft tip are not substantially parallel, linearly moves the implant body towards an insertion end of an outer shaft of the implant insertion device so as to secure the implant body against the insertion end of the outer shaft, delivering the implant body into a subject using the implanting insertion device; reversely rotating the knob of the inner shaft of the implant insertion device in a manner such that the reverse rotation of the knob rotates the inner shaft tip within the main slot in the implant body such that the major axis of the main slot and the major axis of the inner shaft tip are substantially parallel, associates the first interface of the knob to the first complimentary interface at the outer shaft at a second position. In some cases, the methods comprising removing the insertion device from a package. In some cases, the methods comprising fitting a first interface of the knob to a first complementary interface at the outer shaft at a first position. In some cases, the package comprises a first kit cover, or a second kit cover, or a first and a second kit covers. In some cases, the methods comprises fitting a second interface of the implant body to a second complimentary interface at the insertion end of the outer shaft such that the implant body is substantially locked to the insertion device. In some cases, the methods comprises fitting at least one side slot of the implant body to at least one outer shaft tip at the insertion end of the outer shaft such that the implant body is substantially locked to the insertion device In some cases, the methods comprises releasing at least one side slot of the implant body from the at least one outer shaft tip at the insertion end of the outer shaft. In some cases, the method comprises disposing the implant insertion device after a single use. In some cases, the implant insertion device is disposable. In some cases, the implant insertion device is for one-time use only. In some cases, the implant insertion device is injection moldable. In some cases, the first interface comprises at least one side slot indented into the implant body proximal to the main slot, wherein each side slot is configured to receive an outer shaft tip. In some cases, the at least one side slot is peripherally proximal to the main slot. In some cases, the at least one side slot is shallower than the main slot. In some cases, the main slot and the at least one side slot are indented into the supporting structure. In some cases, the main slot is indented deeper into the wall of the implant body than the two side slots along the insertion direction. In some cases, the internal space of the implant body is filled at least partly by at least one graft material. In some cases, the implant body is substantially toroidal. In some cases, the height of the implant body along the anterior-to-posterior direction is configured to accommodate the lordosis angle of the spinal cord when the implant body is properly inserted. In some cases, a toroidal shape is a shape with a plurality of cross sections stacked together continuously, the cross sections being non-uniform in height when properly deployed, and each cross section having an arbitrary two dimensional empty area enclosed by a wall. In some cases, a toroidal shape is a shape comprising a hole in an arbitrary three dimensional volume. In some cases, the internal space is not covered at the top cross section, bottom cross section, or top and bottom cross sections thereof by the implant body. In some cases, the implant body enclosing the internal space has a wall thickness of at least 1 millimeter but no more than 3 centimeters. In some cases, the implant body comprises at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the implant body is injection moldable. In some cases, the implant body is machinable. In some cases, the implant body comprises a saw tooth configured to allow unidirectional insertion into a subject, the saw tooth being on an outer surface of the implant body. In some cases, the saw tooth is further located on the longitudinal plane of the implant body. In some cases, the saw tooth is configured to prevent back-out after insertion of an implant insertion direction. In some cases, the implant body comprises at least one space for accommodating at least one detectable tag. In some cases, the detectable tags comprise radio frequency detectable tags. In some cases, the at least one space are in the wall of the implant body. In some cases, the implant body comprises at least two spaces for detectable tags, the at least two spaces being not greater than 5 mm in their widest dimension. In some cases, the implant body comprises at least two spaces for detectable tags, the at least two spaces are spatially separated from each other. In some cases, the implant body comprises four spaces for detectable tags, spatially separated from each other. In some cases, the cross section of the implant body along the longitudinal plane comprises a closed contour formed by the implant body. In some cases, the closed contour encloses an area therewithin. In some cases, the internal space is enclosed by closed contours in a plurality of adjacent longitudinal planes. In some cases, the cross section of the implant body along a longitudinal plane is a square, a rectangle, a circle, an ellipse, a rhombus, a trapezoid, a pentagon, or an arbitrary two dimensional shape enclosing an empty two dimensional area in a closed contour. In some cases, the cross section of the implant body along a longitudinal plane is a two-dimensional shape similar to a cross section of the intervertebral space to be inserted therein. In some cases, the cross section of the implant body along a longitudinal plane is comprises a closed contour with a non-uniform thickness along the closed contour. In some cases, the non-uniform thickness along the closed contour is filled with at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the chamber of the implant body is connected to a slot indented from a top-most region or a bottom-most region of the outer surface along a longitudinal direction. In some cases, the slot indented from the top-most region or the bottom-most region of the outer surface is configured to facilitate molding of a chamber therewithin. In some cases, the slot is configured to enable visualization of the inner shaft tip. In some cases, the inner shaft is disposable. In some cases, the inner shaft is for one-time use only. In some cases, the inner shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the inner shaft comprises about 50% glass. In some cases, the inner shaft comprises a material having a glass content of at least 10% to no greater than 70%. In some cases, the inner shaft tip comprises at least one metal. In some cases, the inner shaft body comprises at least one metal. In some cases, the inner shaft is injection moldable. In some cases, the inner shaft tip is injection moldable. In some cases, the inner shaft body is injection moldable. In some cases, the knob is injection moldable. In some cases, the inner shaft is injection moldable and machinable. In some cases, the inner shaft body is substantially cylindrical. In some cases, the inner shaft body is flexible so as to fit in a curved outer shaft body. In some cases, the inner shaft body is a cylinder. In some cases, the knob of the inner shaft is not enclosed in the outer shaft. In some cases, the inner shaft tip is not enclosed in the outer shaft. In some cases, the inner shaft tip is connected to the inner shaft body in a manner such that the inner shaft tip rotates concentrically when the inner shaft body rotates. In some cases, the inner shaft tip is attached to the inner shaft body such that the center of the cross section of the inner shaft body overlaps with the middle point of the two foci of the inner shaft tip. In some cases, the linear movement draws the inner shaft tip towards the two outer shaft tips. In some cases, the inner shaft tip is substantially rectangular cuboid or cylindrically elliptical. In some cases, the inner shaft comprises at least two protrusions proximal to the inner shaft tip to ensure concentric rotation of the inner shaft within the outer shaft. In some cases, the at least two protrusions are enclosed in the outer shaft. In some cases, the at least two protrusions contact an inner surface of the outer shaft. In some cases, the first interface comprises a cam feature. In some cases, the cam feature is semi-circular. In some cases, the cam feature is substantially a circle sector, a triangle, a quadrilateral, or a pentagon. In some cases, the cam feature is substantially a circle sector with a central angle of 45, 60, 90, 120, or 150 degrees. In some cases, the cam feature is substantially a circle sector with a central angle of at least 15 degrees to up to 275 degrees. In some cases, the cam feature is substantially a triangle, a quadrilateral, or a pentagon with an angle of at least 15 degrees to up to 150 degrees. In some cases, the cam feature is substantially a triangle, a quadrilateral, or a pentagon with an angle of 65, 75, 85, 95, 105, or 115 degrees. In some cases, the cam feature is attached to the knob of the inner shaft. In some cases, the knob is substantially cylindrical. In some cases, the cross section of the knob is greater than the cross section of the inner shaft body. In some cases, the knob of the inner shaft is configured to not fit into the outer shaft at the base of the outer shaft. In some cases, the knob comprises a hump. In some cases, the hump is configured to unlock the inner shaft from the outer shaft at the first position and lock the inner shaft to the outer shaft at the second position. In some cases, the inner shaft tip is substantially rectangular cuboid or cylindrically elliptical. In some cases, the inner shaft tip is configured to fit and rotate in the chamber of the implant body. In some cases, the inner shaft tip is configured to pass through the outer shaft opening. In some cases, the inner shaft tip is configured to pass through the outer shaft opening only when a major axis of the inner shaft tip and a major axis of the outer shaft opening are substantially parallel. In some cases, the first or the second complimentary interface comprises a cam feature. In some cases, the first or the second interface comprises a first surface and a second surface. In some cases, the first and the second surfaces are displaced by a distance that the inner shaft tip is capable of moving with respect to the outer shaft. In some cases, the first and the second surfaces are displaced by a distance determined by a length and a rising angle of the ramp. In some cases, the first or the second interface comprises at least one slot. In some cases, the first or the second complimentary interface comprises at least a slot. In some cases, the first or the second interface comprises at least one tip or at least two tips. In some cases, the outer shaft is disposable. In some cases, the outer shaft is for one-time use only. In some cases, the outer shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the outer shaft comprises about 50% glass. In some cases, the outer shaft comprises a glass content of at least 10% to no greater than 70%. In some cases, the outer shaft is injection moldable. In some cases, the outer shaft is injection moldable and machinable. In some cases, the cross sectional area of the outer shaft is monotonically non-increasing from a base of the outer shaft to an insertion end of the outer shaft. In some cases, the outer shaft opening is substantially circular. In some cases, the outer shaft opening is configured to allow passage of the inner shaft tip. In some cases, the outer shaft comprises a third interface, wherein the third interface unlocks to the hump at the first position and locks to the hump at the second position. In some cases, the outer shaft comprises at least one insertion stopper on the outer shaft to limit insertion depth into an intervertebral space of the subject. In some cases, the outer shaft comprises at least an insertion stopper attached to the outer shaft. In some cases, the outer shaft comprises at least an insertion stopper, the height of the insertion stopper being greater than 0.2 millimeters but less than 2 centimeters. In some cases, the outer shaft comprises at least a ramped protrusion to prevent the inner shaft from sliding out while the inner shaft is inserted therewithin. In some cases, the outer shaft comprises at least a ramped protrusion so that the inner shaft only comes out of the outer shaft when the implant body is not locked to an inner shaft tip. In some cases, the outer shaft comprises at least a ramped protrusion so that the inner shaft only comes out of the outer shaft when the major axis of the inner shaft tip and the major axis of the main slot of the implant body are substantially perpendicular. In some cases, the outer shaft opening at the insertion end of the outer shaft is further configured to allow passage of the inner shaft tip only when the major axis of the inner shaft tip and the major axis of the outer shaft opening are substantially parallel. In some cases, the first or the second complimentary interface comprises a first surface and a second surface. In some cases, the first surface and the second surface are semi-circular. In some cases, the first surface and the second surface are a portion of a circle sector. In some cases, the first surface and the second surface are a portion of a circle sector with a central angle of at least 15 degrees to up to 275 degrees. In some cases, the first or the second complimentary interface comprises at least one or at least two tips. In some cases, each tip is substantially semi-rectangular cuboid or semi-cylindrically elliptical. In some cases, each tip is peripherally proximal to the outer shaft opening at the insertion end of the outer shaft. In some cases, the at least two tips are symmetrically adjacent to the outer shaft opening at the insertion end of the outer shaft, and on an extension of the major axis of the outer shaft opening. In some cases, each tip is on the outer face of the outer shaft. In some cases, each tip is substantially semi-rectangular cuboid or semi-cylindrically elliptical. In some cases, each tip is configured to fit in one side slot of the implant body when the implant body is locked to the outer shaft. In some cases, the locking the implant body to the inner shaft comprises that a major axis of the main slot and a major axis of the inner shaft tip are not substantially parallel. In some cases, not substantially parallel comprises an angle of about 90 degrees between the major axis of the main slot and a major axis of the inner shaft tip. In some cases, the linear movement of the inner shaft body is determined by a height of the interface or the complimentary interface and a rotation angle that the cam feature rotates from a predetermined location along a circumference of the knob. In some cases, the methods comprises rotating the knob of an inner shaft of the implant insertion device in a manner such that the rotation of the knob linearly displaces the implant body from the insertion end of the outer shaft of the implant insertion device. In some aspects the methods comprise inserting the implant into an intervertebral space. In some aspects the intervertebral space is lumbar. In some aspects the intervertebral space is cervical. In some aspects intervertebral disk material is removed from the intervertebral space prior to inserting the implant. In some aspects the implant is inserted into the interior of an intervertebral disk.

Also disclosed herein, in certain embodiments, are methods for delivering an implant body using an implant insertion device comprising releasing an implant body into an intervertebral space of a patient comprising: rotating a knob of an inner shaft of the implant insertion device in a manner such that a rotation of the knob rotates an inner shaft tip within a main slot in the implant body substantially in a coronal plane such that a major axis of the main slot and a major axis of the inner shaft tip are substantially parallel, and associates a first interface of the knob to a first complimentary interface at an outer shaft at a unlocked position; and depositing the implant body in an intervertebral space of the patient. In some cases, the methods comprises locking the implant body to the implant insertion device by a rotation of a knob of an inner shaft of the implant insertion device in a manner such that the rotation of the knob rotates an inner shaft tip within a chamber of the implant body substantially in a coronal plane such that a major axis of the main slot and a major axis of the inner shaft tip are not substantially parallel, linearly moves the implant body towards an insertion end of the outer shaft of the implant insertion device so as to secure the implant body against the insertion end of the outer shaft, and associates the first interface of the knob to the first complementary interface at the outer shaft at the first position. In some cases, the methods comprising removing the insertion device from a package. In some cases, the methods comprising fitting a first interface of the knob to a first complementary interface at the outer shaft at a first position. In some cases, the package comprises a first kit cover, or a second kit cover, or a first and a second kit covers. In some cases, the methods comprises fitting a second interface of the implant body to a second complimentary interface at the insertion end of the outer shaft such that the implant body is substantially locked to the insertion device. In some cases, the methods comprises fitting at least one side slot of the implant body to at least one outer shaft tip at the insertion end of the outer shaft such that the implant body is substantially locked to the insertion device In some cases, the methods comprises releasing at least one side slot of the implant body from the at least one outer shaft tip at the insertion end of the outer shaft. In some cases, the method comprises disposing the implant insertion device after a single use. In some cases, the implant insertion device is disposable. In some cases, the implant insertion device is for one-time use only. In some cases, the implant insertion device is injection moldable. In some cases, the first interface comprises at least one side slot indented into the implant body proximal to the main slot, wherein each side slot is configured to receive an outer shaft tip. In some cases, the at least one side slot is peripherally proximal to the main slot. In some cases, the at least one side slot is shallower than the main slot. In some cases, the main slot and the at least one side slot are indented into the supporting structure. In some cases, the main slot is indented deeper into the wall of the implant body than the two side slots along the insertion direction. In some cases, the internal space of the implant body is filled at least partly by at least one graft material. In some cases, the implant body is substantially toroidal. In some cases, the height of the implant body along the anterior-to-posterior direction is configured to accommodate the lordosis angle of the spinal cord when the implant body is properly inserted. In some cases, a toroidal shape is a shape with a plurality of cross sections stacked together continuously, the cross sections being non-uniform in height when properly deployed, and each cross section having an arbitrary two dimensional empty area enclosed by a wall. In some cases, a toroidal shape is a shape comprising a hole in an arbitrary three dimensional volume. In some cases, the internal space is not covered at the top cross section, bottom cross section, or top and bottom cross sections thereof by the implant body. In some cases, the implant body enclosing the internal space has a wall thickness of at least 1 millimeter but no more than 3 centimeters. In some cases, the implant body comprises at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the implant body is injection moldable. In some cases, the implant body is machinable. In some cases, the implant body comprises a saw tooth configured to allow unidirectional insertion into a subject, the saw tooth being on an outer surface of the implant body. In some cases, the saw tooth is further located on the longitudinal plane of the implant body. In some cases, the saw tooth is configured to prevent back-out after insertion of an implant insertion direction. In some cases, the implant body comprises at least one space for accommodating at least one detectable tag. In some cases, the detectable tags comprise radio frequency detectable tags. In some cases, the at least one space are in the wall of the implant body. In some cases, the implant body comprises at least two spaces for detectable tags, the at least two spaces being not greater than 5 mm in their widest dimension. In some cases, the implant body comprises at least two spaces for detectable tags, the at least two spaces are spatially separated from each other. In some cases, the implant body comprises four spaces for detectable tags, spatially separated from each other. In some cases, the cross section of the implant body along the longitudinal plane comprises a closed contour formed by the implant body. In some cases, the closed contour encloses an area therewithin. In some cases, the internal space is enclosed by closed contours in a plurality of adjacent longitudinal planes. In some cases, the cross section of the implant body along a longitudinal plane is a square, a rectangle, a circle, an ellipse, a rhombus, a trapezoid, a pentagon, or an arbitrary two dimensional shape enclosing an empty two dimensional area in a closed contour. In some cases, the cross section of the implant body along a longitudinal plane is a two-dimensional shape similar to a cross section of the intervertebral space to be inserted therein. In some cases, the cross section of the implant body along a longitudinal plane is comprises a closed contour with a non-uniform thickness along the closed contour. In some cases, the non-uniform thickness along the closed contour is filled with at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the chamber of the implant body is connected to a slot indented from a top-most region or a bottom-most region of the outer surface along a longitudinal direction. In some cases, the slot indented from the top-most region or the bottom-most region of the outer surface is configured to facilitate molding of a chamber therewithin. In some cases, the slot is configured to enable visualization of the inner shaft tip. In some cases, the inner shaft is disposable. In some cases, the inner shaft is for one-time use only. In some cases, the inner shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the inner shaft comprises about 50% glass. In some cases, the inner shaft comprises a material having a glass content of at least 10% to no greater than 70%. In some cases, the inner shaft tip comprises at least one metal. In some cases, the inner shaft body comprises at least one metal. In some cases, the inner shaft is injection moldable. In some cases, the inner shaft tip is injection moldable. In some cases, the inner shaft body is injection moldable. In some cases, the knob is injection moldable. In some cases, the inner shaft is injection moldable and machinable. In some cases, the inner shaft body is substantially cylindrical. In some cases, the inner shaft body is flexible so as to fit in a curved outer shaft body. In some cases, the inner shaft body is a cylinder. In some cases, the knob of the inner shaft is not enclosed in the outer shaft. In some cases, the inner shaft tip is not enclosed in the outer shaft. In some cases, the inner shaft tip is connected to the inner shaft body in a manner such that the inner shaft tip rotates concentrically when the inner shaft body rotates. In some cases, the inner shaft tip is attached to the inner shaft body such that the center of the cross section of the inner shaft body overlaps with the middle point of the two foci of the inner shaft tip. In some cases, the linear movement draws the inner shaft tip towards the two outer shaft tips. In some cases, the inner shaft tip is substantially rectangular cuboid or cylindrically elliptical. In some cases, the inner shaft comprises at least two protrusions proximal to the inner shaft tip to ensure concentric rotation of the inner shaft within the outer shaft. In some cases, the at least two protrusions are enclosed in the outer shaft. In some cases, the at least two protrusions contact an inner surface of the outer shaft. In some cases, the first interface comprises a cam feature. In some cases, the cam feature is semi-circular. In some cases, the cam feature is substantially a circle sector, a triangle, a quadrilateral, or a pentagon. In some cases, the cam feature is substantially a circle sector with a central angle of 45, 60, 90, 120, or 150 degrees. In some cases, the cam feature is substantially a circle sector with a central angle of at least 15 degrees to up to 275 degrees. In some cases, the cam feature is substantially a triangle, a quadrilateral, or a pentagon with an angle of at least 15 degrees to up to 150 degrees. In some cases, the cam feature is substantially a triangle, a quadrilateral, or a pentagon with an angle of 65, 75, 85, 95, 105, or 115 degrees. In some cases, the cam feature is attached to the knob of the inner shaft. In some cases, the knob is substantially cylindrical. In some cases, the cross section of the knob is greater than the cross section of the inner shaft body. In some cases, the knob of the inner shaft is configured to not fit into the outer shaft at the base of the outer shaft. In some cases, the knob comprises a hump. In some cases, the hump is configured to unlock the inner shaft from the outer shaft at the first position and lock the inner shaft to the outer shaft at the second position. In some cases, the inner shaft tip is substantially rectangular cuboid or cylindrically elliptical. In some cases, the inner shaft tip is configured to fit and rotate in the chamber of the implant body. In some cases, the inner shaft tip is configured to pass through the outer shaft opening. In some cases, the inner shaft tip is configured to pass through the outer shaft opening only when a major axis of the inner shaft tip and a major axis of the outer shaft opening are substantially parallel. In some cases, the first or the second complimentary interface comprises a cam feature. In some cases, the first or the second interface comprises a first surface and a second surface. In some cases, the first and the second surfaces are displaced by a distance that the inner shaft tip is capable of moving with respect to the outer shaft. In some cases, the first and the second surfaces are displaced by a distance determined by a length and a rising angle of the ramp. In some cases, the first or the second interface comprises at least one slot. In some cases, the first or the second complimentary interface comprises at least a slot. In some cases, the first or the second interface comprises at least one tip or at least two tips. In some cases, the outer shaft is disposable. In some cases, the outer shaft is for one-time use only. In some cases, the outer shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the outer shaft comprises about 50% glass. In some cases, the outer shaft comprises a glass content of at least 10% to no greater than 70%. In some cases, the outer shaft is injection moldable. In some cases, the outer shaft is injection moldable and machinable. In some cases, the cross sectional area of the outer shaft is monotonically non-increasing from a base of the outer shaft to an insertion end of the outer shaft. In some cases, the outer shaft opening is substantially circular. In some cases, the outer shaft opening is configured to allow passage of the inner shaft tip. In some cases, the outer shaft comprises a third interface, wherein the third interface unlocks to the hump at the first position and locks to the hump at the second position. In some cases, the outer shaft comprises at least one insertion stopper on the outer shaft to limit insertion depth into an intervertebral space of the subject. In some cases, the outer shaft comprises at least an insertion stopper attached to the outer shaft. In some cases, the outer shaft comprises at least an insertion stopper, the height of the insertion stopper being greater than 0.2 millimeters but less than 2 centimeters. In some cases, the outer shaft comprises at least a ramped protrusion to prevent the inner shaft from sliding out while the inner shaft is inserted therewithin. In some cases, the outer shaft comprises at least a ramped protrusion so that the inner shaft only comes out of the outer shaft when the implant body is not locked to an inner shaft tip. In some cases, the outer shaft comprises at least a ramped protrusion so that the inner shaft only comes out of the outer shaft when the major axis of the inner shaft tip and the major axis of the main slot of the implant body are substantially perpendicular. In some cases, the outer shaft opening at the insertion end of the outer shaft is further configured to allow passage of the inner shaft tip only when the major axis of the inner shaft tip and the major axis of the outer shaft opening are substantially parallel. In some cases, the first or the second complimentary interface comprises a first surface and a second surface. In some cases, the first surface and the second surface are semi-circular. In some cases, the first surface and the second surface are a portion of a circle sector. In some cases, the first surface and the second surface are a portion of a circle sector with a central angle of at least 15 degrees to up to 275 degrees. In some cases, the first or the second complimentary interface comprises at least one or at least two tips. In some cases, each tip is substantially semi-rectangular cuboid or semi-cylindrically elliptical. In some cases, each tip is peripherally proximal to the outer shaft opening at the insertion end of the outer shaft. In some cases, the at least two tips are symmetrically adjacent to the outer shaft opening at the insertion end of the outer shaft, and on an extension of the major axis of the outer shaft opening. In some cases, each tip is on the outer face of the outer shaft. In some cases, each tip is substantially semi-rectangular cuboid or semi-cylindrically elliptical. In some cases, each tip is configured to fit in one side slot of the implant body when the implant body is locked to the outer shaft. In some cases, the locking the implant body to the inner shaft comprises that a major axis of the main slot and a major axis of the inner shaft tip are not substantially parallel. In some cases, not substantially parallel comprises an angle of about 90 degrees between the major axis of the main slot and a major axis of the inner shaft tip. In some cases, the linear movement of the inner shaft body is determined by a height of the interface or the complimentary interface and a rotation angle that the cam feature rotates from a predetermined location along a circumference of the knob. In some cases, the methods comprises rotating the knob of an inner shaft of the implant insertion device in a manner such that the rotation of the knob linearly displaces the implant body from the insertion end of the outer shaft of the implant insertion device. In some aspects the methods comprise inserting the implant into an intervertebral space. In some aspects the intervertebral space is lumbar. In some aspects the intervertebral space is cervical. In some aspects intervertebral disk material is removed from the intervertebral space prior to inserting the implant. In some aspects the implant is inserted into the interior of an intervertebral disk.

Also disclosed herein, in certain cases, are sterile kits containing a single-use implant body insertion device and a single use implant, the sterile kit comprising: a sterile kit cover sealed to enclose at least one device tray, at least one implant body, and at least one implant insertion device therewithin, wherein the at least one implant body and the at least one implant insertion device are configured for a single usage; the at least one device tray is configured to secure: the at least one implant insertion device; the at least one implant body; the at least one implant insertion device comprising: a shaft; a tip; a first interface for locking the at least one implant body; a second interface for locking the at least one implant body; a first position; a second position; and the at least one implant body comprising: an internal space; a slot for locking the at least one implant body against the at least one implant insertion device at the first position; a first complimentary interface for receiving the interface of the at least one implant insertion device at the first position or the second position; a second complimentary interface for receiving the second interface of the at least one implant insertion device at the first position. In some cases, the kit comprises a second kit cover sealed to enclose the sterile kit cover. In some cases, the second kit cover is sterile. In some cases, the device tray comprises a compartment to secure at least one implant body to facilitate loading at least one graft material to the internal space thereof. In some cases, the kits comprising removing the insertion device from a package. In some cases, the kits comprising fitting a first interface of the knob to a first complementary interface at the outer shaft at a first position. In some cases, the package comprises a first kit cover, or a second kit cover, or a first and a second kit covers. In some cases, the kits comprises fitting a second interface of the implant body to a second complimentary interface at the insertion end of the outer shaft such that the implant body is substantially locked to the insertion device. In some cases, the kits comprises fitting at least one side slot of the implant body to at least one outer shaft tip at the insertion end of the outer shaft such that the implant body is substantially locked to the insertion device In some cases, the kits comprises releasing at least one side slot of the implant body from the at least one outer shaft tip at the insertion end of the outer shaft. In some cases, the kit comprises disposing the implant insertion device after a single use. In some cases, the implant insertion device is disposable. In some cases, the implant insertion device is for one-time use only. In some cases, the implant insertion device is injection moldable. In some cases, the first interface comprises at least one side slot indented into the implant body proximal to the main slot, wherein each side slot is configured to receive an outer shaft tip. In some cases, the at least one side slot is peripherally proximal to the main slot. In some cases, the at least one side slot is shallower than the main slot. In some cases, the main slot and the at least one side slot are indented into the supporting structure. In some cases, the main slot is indented deeper into the wall of the implant body than the two side slots along the insertion direction. In some cases, the internal space of the implant body is filled at least partly by at least one graft material. In some cases, the implant body is substantially toroidal. In some cases, the height of the implant body along the anterior-to-posterior direction is configured to accommodate the lordosis angle of the spinal cord when the implant body is properly inserted. In some cases, a toroidal shape is a shape with a plurality of cross sections stacked together continuously, the cross sections being non-uniform in height when properly deployed, and each cross section having an arbitrary two dimensional empty area enclosed by a wall. In some cases, a toroidal shape is a shape comprising a hole in an arbitrary three dimensional volume. In some cases, the internal space is not covered at the top cross section, bottom cross section, or top and bottom cross sections thereof by the implant body. In some cases, the implant body enclosing the internal space has a wall thickness of at least 1 millimeter but no more than 3 centimeters. In some cases, the implant body comprises at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the implant body is injection moldable. In some cases, the implant body is machinable. In some cases, the implant body comprises a saw tooth configured to allow unidirectional insertion into a subject, the saw tooth being on an outer surface of the implant body. In some cases, the saw tooth is further located on the longitudinal plane of the implant body. In some cases, the saw tooth is configured to prevent back-out after insertion of an implant insertion direction. In some cases, the implant body comprises at least one space for accommodating at least one detectable tag. In some cases, the detectable tags comprise radio frequency detectable tags. In some cases, the at least one space are in the wall of the implant body. In some cases, the implant body comprises at least two spaces for detectable tags, the at least two spaces being not greater than 5 mm in their widest dimension. In some cases, the implant body comprises at least two spaces for detectable tags, the at least two spaces are spatially separated from each other. In some cases, the implant body comprises four spaces for detectable tags, spatially separated from each other. In some cases, the cross section of the implant body along the longitudinal plane comprises a closed contour formed by the implant body. In some cases, the closed contour encloses an area therewithin. In some cases, the internal space is enclosed by closed contours in a plurality of adjacent longitudinal planes. In some cases, the cross section of the implant body along a longitudinal plane is a square, a rectangle, a circle, an ellipse, a rhombus, a trapezoid, a pentagon, or an arbitrary two dimensional shape enclosing an empty two dimensional area in a closed contour. In some cases, the cross section of the implant body along a longitudinal plane is a two-dimensional shape similar to a cross section of the intervertebral space to be inserted therein. In some cases, the cross section of the implant body along a longitudinal plane is comprises a closed contour with a non-uniform thickness along the closed contour. In some cases, the non-uniform thickness along the closed contour is filled with at least one selected from polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK). In some cases, the chamber of the implant body is connected to a slot indented from a top-most region or a bottom-most region of the outer surface along a longitudinal direction. In some cases, the slot indented from the top-most region or the bottom-most region of the outer surface is configured to facilitate molding of a chamber therewithin. In some cases, the slot is configured to enable visualization of the inner shaft tip. In some cases, the inner shaft is disposable. In some cases, the inner shaft is for one-time use only. In some cases, the inner shaft comprises at least one selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the inner shaft comprises about 50% glass. In some cases, the inner shaft comprises a material having a glass content of at least 10% to no greater than 70%. In some cases, the inner shaft tip comprises at least one metal. In some cases, the inner shaft body comprises at least one metal. In some cases, the inner shaft is injection moldable. In some cases, the inner shaft tip is injection moldable. In some cases, the inner shaft body is injection moldable. In some cases, the knob is injection moldable. In some cases, the inner shaft is injection moldable and machinable. In some cases, the inner shaft body is substantially cylindrical. In some cases, the inner shaft body is flexible so as to fit in a curved outer shaft body. In some cases, the inner shaft body is a cylinder. In some cases, the knob of the inner shaft is not enclosed in the outer shaft. In some cases, the inner shaft tip is not enclosed in the outer shaft. In some cases, the inner shaft tip is connected to the inner shaft body in a manner such that the inner shaft tip rotates concentrically when the inner shaft body rotates. In some cases, the inner shaft tip is attached to the inner shaft body such that the center of the cross section of the inner shaft body overlaps with the middle point of the two foci of the inner shaft tip. In some cases, the linear movement draws the inner shaft tip towards the two outer shaft tips. In some cases, the inner shaft tip is substantially rectangular cuboid or cylindrically elliptical. In some cases, the inner shaft comprises at least two protrusions proximal to the inner shaft tip to ensure concentric rotation of the inner shaft within the outer shaft. In some cases, the at least two protrusions are enclosed in the outer shaft. In some cases, the at least two protrusions contact an inner surface of the outer shaft. In some cases, the first interface comprises a cam feature. In some cases, the cam feature is semi-circular. In some cases, the cam feature is substantially a circle sector, a triangle, a quadrilateral, or a pentagon. In some cases, the cam feature is substantially a circle sector with a central angle of 45, 60, 90, 120, or 150 degrees. In some cases, the cam feature is substantially a circle sector with a central angle of at least 15 degrees to up to 275 degrees. In some cases, the cam feature is substantially a triangle, a quadrilateral, or a pentagon with an angle of at least 15 degrees to up to 150 degrees. In some cases, the cam feature is substantially a triangle, a quadrilateral, or a pentagon with an angle of 65, 75, 85, 95, 105, or 115 degrees. In some cases, the cam feature is attached to the knob of the inner shaft. In some cases, the knob is substantially cylindrical. In some cases, the cross section of the knob is greater than the cross section of the inner shaft body. In some cases, the knob of the inner shaft is configured to not fit into the outer shaft at the base of the outer shaft. In some cases, the knob comprises a hump. In some cases, the hump is configured to unlock the inner shaft from the outer shaft at the first position and lock the inner shaft to the outer shaft at the second position. In some cases, the inner shaft tip is substantially rectangular cuboid or cylindrically elliptical. In some cases, the inner shaft tip is configured to fit and rotate in the chamber of the implant body. In some cases, the inner shaft tip is configured to pass through the outer shaft opening. In some cases, the inner shaft tip is configured to pass through the outer shaft opening only when a major axis of the inner shaft tip and a major axis of the outer shaft opening are substantially parallel. In some cases, the first or the second complimentary interface comprises a cam feature. In some cases, the first or the second interface comprises a first surface and a second surface. In some cases, the first and the second surfaces are displaced by a distance that the inner shaft tip is capable of moving with respect to the outer shaft. In some cases, the first and the second surfaces are displaced by a distance determined by a length and a rising angle of the ramp. In some cases, the first or the second interface comprises at least one slot. In some cases, the first or the second complimentary interface comprises at least a slot. In some cases, the first or the second interface comprises at least one tip. In some cases, the outer shaft is disposable. In some cases, the outer shaft is for one-time use only. In some cases, the outer shaft comprises at least one material selected from carbon fiber-reinforced polymer, carbon fiber-reinforced plastic, carbon fiber-reinforced thermoplastic, glass fiber-reinforced polymer, glass fiber-reinforced plastic, and polyarylamide. In some cases, the outer shaft comprises about 50% glass or 50% glass. In some cases, the outer shaft comprises a glass content of at least 10% to no greater than 70%. In some cases, the outer shaft is injection moldable. In some cases, the outer shaft is injection moldable and machinable. In some cases, the cross sectional area of the outer shaft is monotonically non-increasing from a base of the outer shaft to an insertion end of the outer shaft. In some cases, the outer shaft opening is substantially circular. In some cases, the outer shaft opening allows passage of the inner shaft tip. In some cases, the outer shaft comprises a third interface, wherein the third interface unlocks to the hump at the first position and locks to the hump at the second position. In some cases, the outer shaft comprises at least one insertion stopper on the outer shaft to limit insertion depth into an intervertebral space of the subject. In some cases, the outer shaft comprises at least an insertion stopper attached to the outer shaft. In some cases, the outer shaft comprises at least an insertion stopper, the height of the insertion stopper being greater than 0.2 millimeters but less than 2 centimeters. In some cases, the outer shaft comprises at least a ramped protrusion to prevent the inner shaft from sliding out while the inner shaft is inserted therewithin. In some cases, the outer shaft comprises at least a ramped protrusion so that the inner shaft only comes out of the outer shaft when the implant body is not locked to an inner shaft tip. In some cases, the outer shaft comprises at least a ramped protrusion so that the inner shaft only comes out of the outer shaft when the major axis of the inner shaft tip and the major axis of the main slot of the implant body are substantially perpendicular. In some cases, the outer shaft opening at the insertion end of the outer shaft is further configured to allow passage of the inner shaft tip only when the major axis of the inner shaft tip and the major axis of the outer shaft opening are substantially parallel. In some cases, the first or the second complimentary interface comprises a first surface and a second surface. In some cases, the first surface and the second surface are semi-circular. In some cases, the first surface and the second surface are a portion of a circle sector. In some cases, the first surface and the second surface are a portion of a circle sector with a central angle of at least 15 degrees to up to 275 degrees. In some cases, the first or the second complimentary interface comprises at least one or at least two tips. In some cases, each tip is substantially semi-rectangular cuboid or semi-cylindrically elliptical. In some cases, each tip is peripherally proximal to the outer shaft opening at the insertion end of the outer shaft. In some cases, the at least two tips are symmetrically adjacent to the outer shaft opening at the insertion end of the outer shaft, and on an extension of the major axis of the outer shaft opening. In some cases, each tip is on the outer face of the outer shaft. In some cases, each tip is substantially semi-rectangular cuboid or semi-cylindrically elliptical. In some cases, each tip is configured to fit in one side slot of the implant body when the implant body is locked to the outer shaft. In some cases, the locking the implant body to the inner shaft comprises that a major axis of the main slot and a major axis of the inner shaft tip are not substantially parallel. In some cases, not substantially parallel comprises an angle of about 90 degrees between the major axis of the main slot and a major axis of the inner shaft tip. In some cases, linear movement of the inner shaft body is determined by a height of the interface or the complimentary interface and a rotation angle that the cam feature rotates from a predetermined location along a circumference of the knob. In some cases, the methods comprise rotating the knob of an inner shaft of the implant insertion device in a manner such that the rotation of the knob linearly displaces the implant body from the insertion end of the outer shaft of the implant insertion device.

CERTAIN TERMINOLOGIES

Unless otherwise defined, all technical terms used herein have the same meaning as commonly understood by one of ordinary skills in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Overview:

The systems, methods, devices, and kits disclosed herein includes injection moldable implant insertion devices and implant bodies can be injection molded using one or more durable materials at a lower price than their machinable equivalents. In addition, the injection moldable implant insertion devices and implant bodies are easily made and can be deployed for single use only, so that the contamination associated with cleaning, autoclaving, sterilization, transportation, or maintenance of the machined equivalents are significantly reduced or completely eliminated. The cost of the implant insertion device and implant body per usage is significantly lower than the machined equivalent. Further, injection moldable implant insertion devices and implants can be packed in sterile and peelably sealed kit to prevent contamination and facilitate surgical needs in different medical procedures. Further, the systems, methods, devices, and kits disclosed herein includes at least one secure locking mechanism that locks the implant body to both the inner shaft and the outer shaft of the implant delivery device. Such locking mechanism greatly reduces undesired release or breakage of the implant body from the insertion device. Additional sawtooth features on the implant body also assist the unidirectional insertion during implant delivery. Further, the implant body has a supporting structure that is durable and compatible with biomaterial delivery and anchoring in the patient.

FIG. 1a shows a non-limiting exemplary embodiment of an implant insertion device with an implant body properly locked thereon. The implant body has an outer shaft 20 and an inner shaft 30 with a knob at the base of the insertion device. The outer shaft 20 has an insertion stopper 21 close to the insertion end of the device. The implant body 10 is locked to the inner shaft 30 and attached to the outer shaft 20. The inner shaft has an internal space 11 and a support structure 12 enclosing the internal space. In some cases, the outer shaft 20 is a rod shape with non-uniform cross sectional areas along its longest direction. In some cases, the outer shaft is a curved or bent shaft. In some cases, the outer shaft is flexible. In some cases, the outer shaft is deformable and allows user-defined shaping of its curvature. In some cases, the inner shaft 30 is partly enclosed in the outer shaft 20. In some cases, the knob and the inner shaft tip is not enclosed in the outer shaft 20. In some cases, the inner shaft is flexible. In some cases, the inner shaft body rotates concentrically or non-concentrically in the outer shaft. In some cases, the implant body 10 comprises an arbitrary three-dimensional shape that fits into an intervertebral space of a subject. In some cases, the interface of the implant body 10 to the implant insertion device is on any part of the outer surface of the support structure 12, the interface being configured to lock and/or attached the implant body to the inner shaft 30 and/or outer shaft 20. The insertion stopper 21 is an optional feature of the outer shaft 20. In some cases, the insertion stopper 21 facilitates implant insertion at certain insertion angles with respect to the spinal cord of the patient.

Figure 1B:
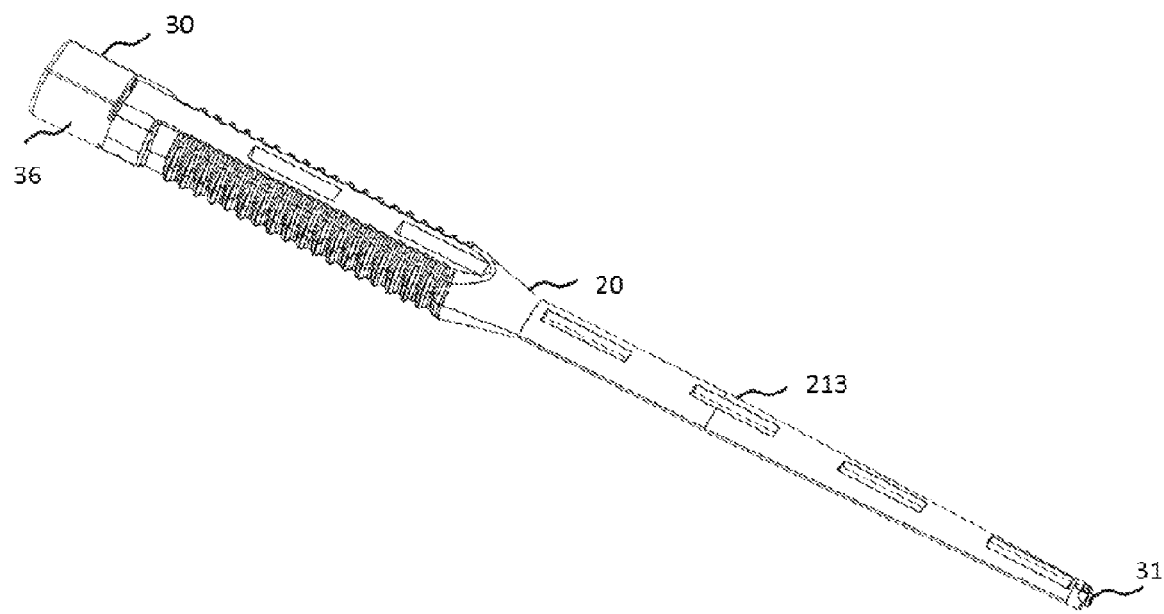
FIG. 1b shows an embodiment of the implant insertion device.

FIG. 1b shows a non-limiting exemplary embodiment of an implant insertion device without an implant body properly locked thereon. The implant body has an outer shaft 20 and an inner shaft 30 with a knob 36 at the base of the insertion device. The inner shaft 30 is partly enclosed in the outer shaft, the inner shaft tip 31 is not enclosed in the outer shaft 20 when it is properly inserted therewithin. The inner shaft tip 31 is in an unlocked position with respect to an implant body that can be loaded thereon. The outer shaft includes a plurality of windows 213 on its outer surface. In some cases, the outer shaft 20 is a rod shape with non-uniform cross sectional areas along its longest direction. In some cases, the outer shaft is a curved or bent shaft. In some cases, the outer shaft is flexible. In some cases, the outer shaft is deformable and allows user-defined shaping of its curvature. In some cases, the inner shaft 30 is partly enclosed in the outer shaft 20. In some cases, the knob and the inner shaft tip is not enclosed in the outer shaft 20. In some cases, the inner shaft 30 is flexible. In some cases, the inner shaft body rotates concentrically or non-concentrically in the outer shaft 20.

Figure 2:
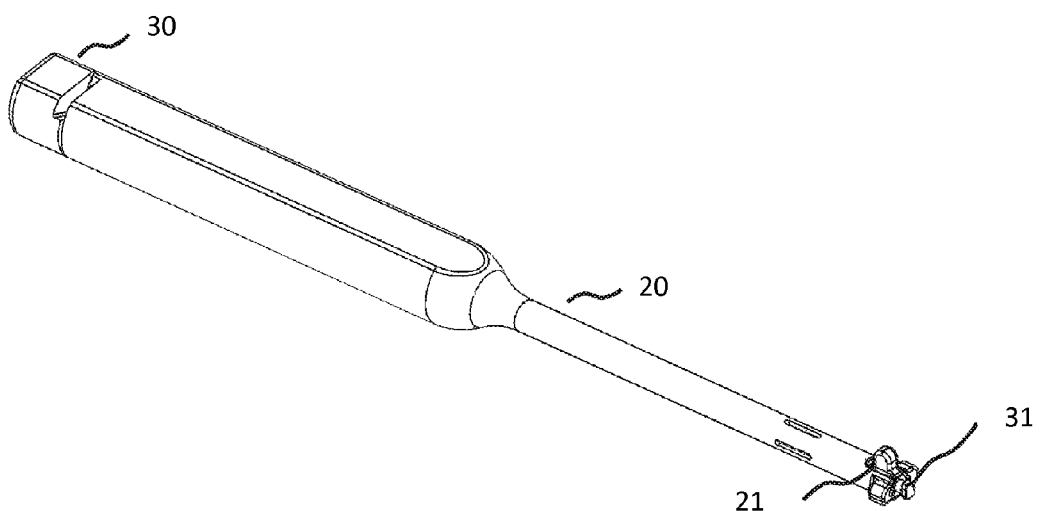
FIG. 2 shows an embodiment of the implant insertion device.

Referring to FIG. 2, in a particular embodiment, an implant insertion device is shown with no implant body attached thereon. The outer shaft 20 has an insertion stopper 21 close to the insertion end of the device. The inner shaft fits through the hollow space of the outer shaft and the inner shaft tip 31 and the knob at the base of the inner shaft 30 is not enclosed within the outer shaft 20.

Implant Shapes:

In some embodiments, the implant body has a cylindrical shape. In some cases, the implant body has a cylindrical shape with cross section of a trapezoid. In other embodiment, the implant body has a cuboid shape. In other embodiment, the implant body has a rectangular cuboid shape. In some cases, the implant body has a cylindrically elliptical shape. In some cases, the implant body is properly shaped to endure the force, pressure, or wear after insertion for a pre-determined period of time. In some cases, the implant body is properly shaped in three spatial dimensions so that it fits into an intervertebral space. In some cases, the implant body has a toroidal shape. In some cases, the support structure has a toroidal shape. A toroidal shape is an arbitrary three dimensional volume having a hole or a three dimensional empty space therethrough. In some cases, a toroidal shape is an arbitrary three dimensional volume having a hole or empty passage therethrough. In some cases, a toroidal shape is a three dimensional ring with some of the circular shapes of the ring replaced by arbitrary two dimensional shapes. In some cases, a toroidal shape is a shape with a plurality of two dimensional cross sections stacked together continuously, the cross sections being non-uniform in height, and each cross section having an arbitrary two dimensional empty area enclosed by a wall. In some cases, the wall has a closed contour and a non-uniform radial thickness along its contour.

In some embodiments, the height of the implant body in uniform. In other cases, the height of the implant body is non-uniform. In some cases, the height of the implant body is non-uniform along the anterior-to-posterior direction when the implant body is properly inserted. In some cases, the non-uniform height of the implant body is structured to accommodate the height difference in an intervertebral space caused by a lordosis angle or kyphosis angle of the spinal column. In some cases, the height of the implant body is smaller at the anterior side of the implant body than the posterior side of the implant body when the implant body is properly inserted. In some cases, the height gradually decreases from the posterior side to the anterior side of the implant body when properly deployed. In other cases, the height gradually increases from the posterior side to the anterior side of the implant body when properly deployed. In some cases, the height of the implant body includes the height of at least one sawtooth. In some cases, the height of the implant body excludes the height of all the sawteeth. In some cases, the sawtooth prevents the implant body from backing out. In some cases, the sawtooth prevents the implant body from sliding or moving after it is properly inserted or located. In some cases, the sawteeth are located on the top-most surface of the support structure and/or the bottom-most surface of the support structure. In exemplary cases, the hole or empty passage is configured to accommodate graft tissue to be inserted therewith.

Figure 3:
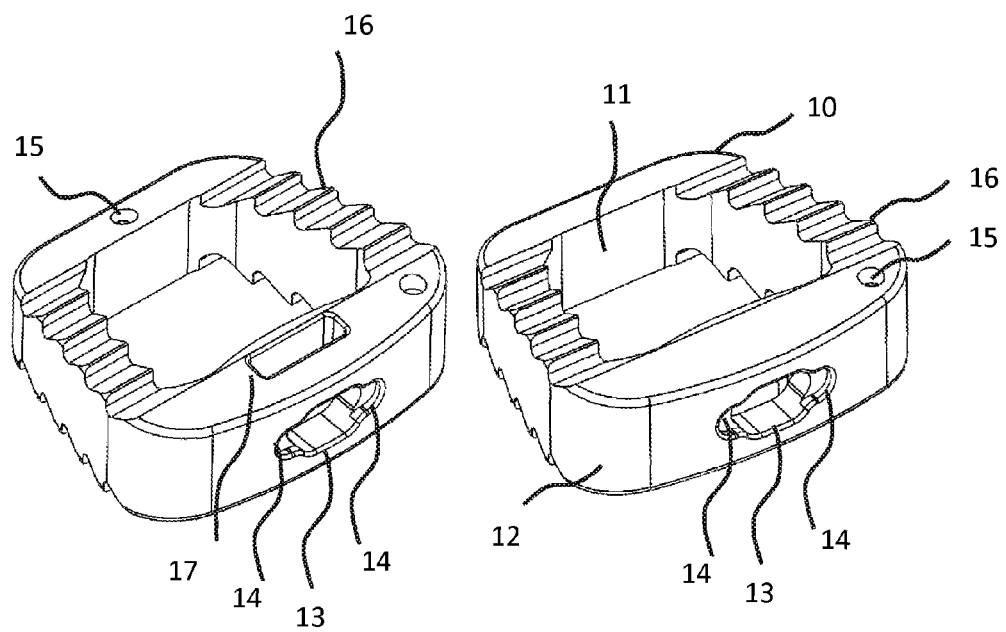
FIG. 3 shows an embodiment of the implant body.

Referring to FIG. 3, in a particular embodiment, an implant body 10 is shown. Image on the left is a top view of the implant body. Image on the right is a bottom view of the implant body. The implant body includes sawteeth 16 on the top and the bottom surfaces. The implant body has a main slot 13 indented from the side of the support structure. Two side slots 14 are symmetrically located proximal to the main slot 13 and shallower than the main slot 13 on the side wall of the implant body 10. The implant body has an internal space 11 that can be filled by graft materials. Spatially separated empty spaces 15 are located in the support structure to enclose detectable tags, such as RF tags therewithin. A top slot 17 connects to the chamber that is accessible from the main slot 13. The implant body has a non-uniform height. In some cases, the side slots 14 are immediately adjacent to the main slot 13. In some cases, the side slots 314 are spatially separated from the main slot 13. In some cases, the implant body 10 has a ring shape. In some cases, the implant body 10 has a donut shape. In some cases, the implant body is toroidal. In some cases, the implant body 10 has a three-dimensional volume with an internal space enclosed in the volume, the internal space accessible from the outer surface of the volume. In some cases, the main slot 13 of the implant body is a cylindrical shape. In some cases, a cross section of the main slot 13 is an ellipse. In some cases, a cross section of the main slot is rectangular. In some cases, a cross section of the main slot is rhombus. In some cases, a cross section of the main slot is triangular. In some cases, the cross section of the main slot is a parallelogram. In some cases, a cross section of the main slot is a cross. In some cases, a main slot of the implant body is indented from an outer surface of the implant body. In some cases, a main slot is indented from an outer surface towards an inner surface of the implant body in a direction that is parallel to the proper implant insertion direction. In some cases, the implant body has no empty spaces 15. In some cases, the implant body has at least one empty spaces 15.

Figure 4:
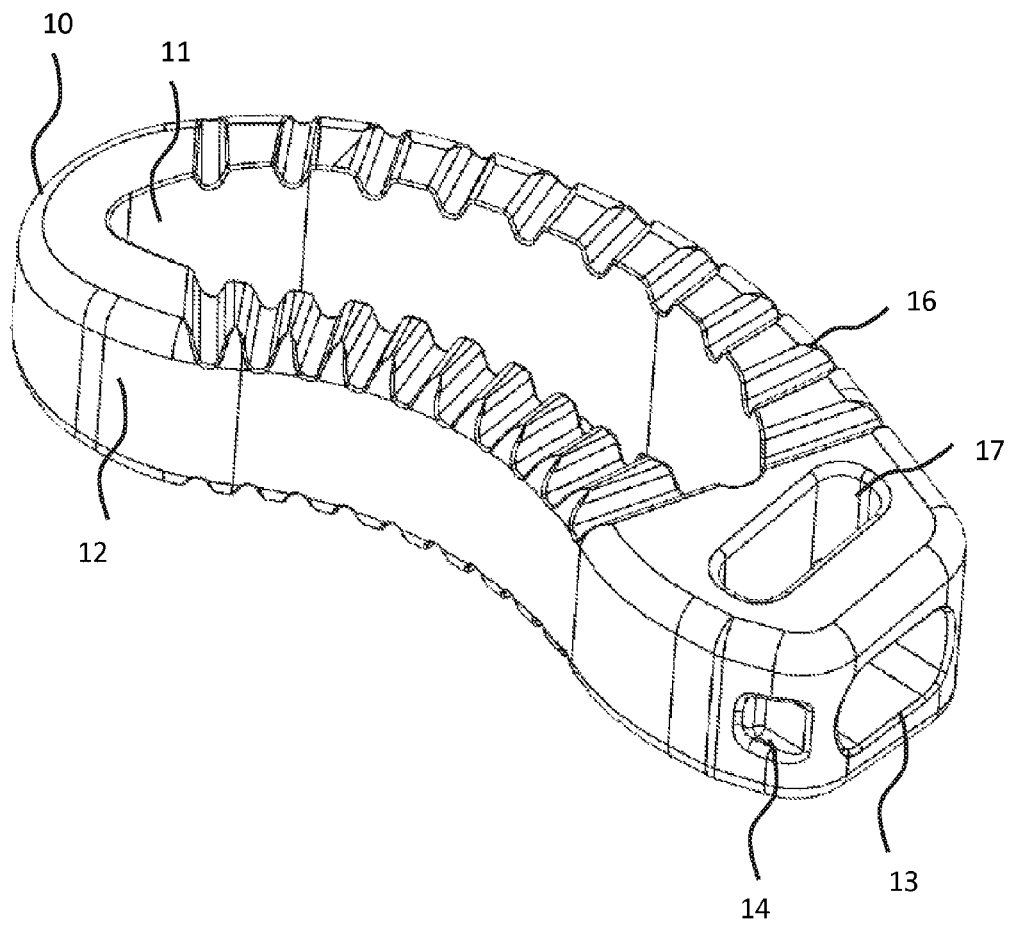
FIG. 4 shows an embodiment of the implant body.

Referring to FIG. 4, in a particular embodiment, an implant body is shown. The implant body has a support structure 12 that encloses an internal space 11 that can be filled by graft materials. The implant body has a main slot 13 indented from the side of the support structure. Two side slots 14 are symmetrically located proximal to the main slot 13 on the side wall of the implant body 10. A top slot 17 connects to the chamber that is accessible from the main slot 13. The implant body 10 includes sawteeth 16 on the top and the bottom surfaces. The implant body has a non-uniform height. The wall thickness of the support structure is not uniform in order to accommodate the lordosis angle of the human spine.

Injection Molded:

As used herein, 'injection molded' refers to being manufactured by a process involving injection or pressure-driven introduction of a non-solid material into a cavity formed by a mold such that, when solidified, the material assumes to form defined by the cavity of the mold. Similarly, 'injection moldable' means capable of being manufactured by such a process. In some cases the terms are used interchangeably. In various cases, the implant insertion devices and implant bodies disclosed herein are injection molded. In some cases, the implant insertion device is injection molded separately. In some cases, the inner shaft of the implant insertion device and the outer shaft of the implant insertion device are injection molded separately. In some cases, the parts of the inner shaft of the implant insertion device are molded separately, wherein the parts includes an inner shaft body, an inner shaft knob, an inner shaft tip. In some cases, the parts of the outer shaft of the implant insertion device are molded separately, wherein the parts includes two outer shaft tips, an outer shaft body excluding the outer shaft tips.

Figure 5:
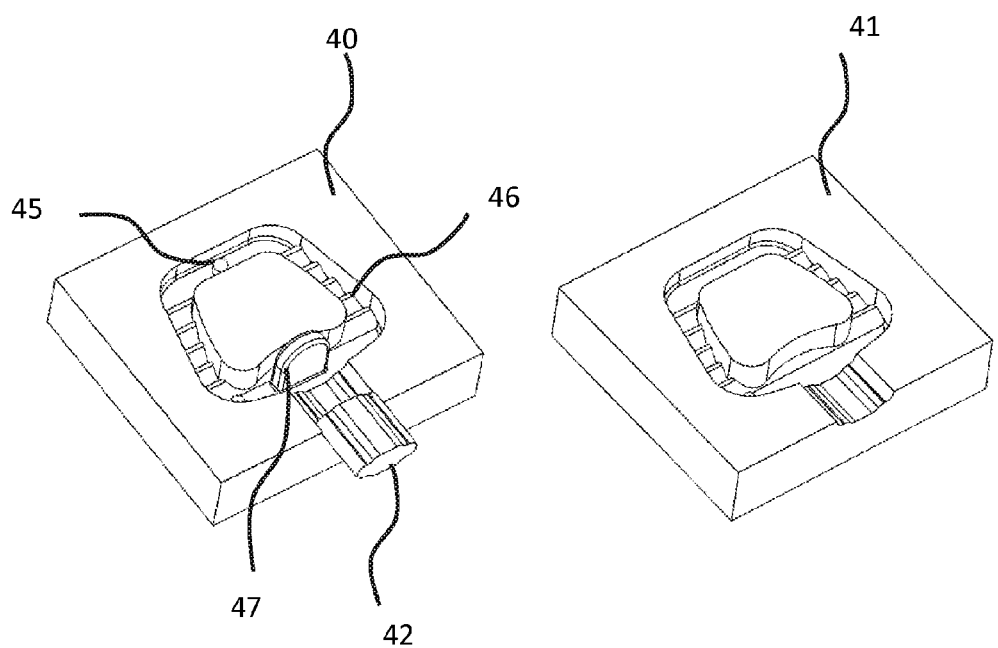
FIG. 5 shows a 3-part mold that is used to mold the embodiment shown in FIG. 3

Referring to FIG. 5, in a particular embodiment, a 3-part mold with parts 40, 41, and 42 are used to mold the implant body in FIG. 3. The mold part 42 slides and out of the mold parts 40 and 41 to form the slots cavity. The mold part 40 includes a U shaped protruding feature 47 to create the cavity of the chamber. The mold part 40 includes a cylindrical protruding feature 45 to create an empty space to load at least a detectable tag. The mold parts 40 and 41 include a feature 46 to create sawteeth on the top and bottom surfaces of the implant body.

Single Use:

As used herein, 'single use' refers to use once only, or in a single procedure on a single patient, or in a single operation. 'Single use' implies that the object does not need to be re-sterilized or reused, as it is discarded rather than being used in a second procedure that may require sterilization prior to use. Single use implies use for delivery of a single implant, or use in delivery of an insert such as an insert comprising graft material in a single intervertebral space, or rarely use in delivery of a first insert comprising a first graft to a first intervertebral space and a second insertion comprising a second graft into a second intervertebral space of a single individual in a single operation. In some cases, implant insertion devices and implant bodies disclosed herein are disposable. In some cases, implant insertion devices and implant bodies disclosed herein are for one-time use only. In some cases, implant insertion devices and implant bodies disclosed herein are not for reuses. In some cases, implant insertion devices and implant bodies disclosed herein are not to be autoclaved. In some cases, implant insertion devices and implant bodies disclosed herein are not for sterilization. Rather devices disclosed herein may in some cases be made cheaply enough that they may be used a single time and disposed of rather than being re used. In some cases, the cost of manufacturing a device herein is less than the cost of sterilization of a machine manufactured device. In many cases, the material is injection moldable such at the device can be made by injecting the material into a mold.

Materials:

In some embodiments, the implant insertion device or the implant body is made of at least one non-metal material. In some cases, the implant insertion device or the implant body is made of at least one metal material. In some cases, the implant insertion device or the implant body is made of at least one plastic material. In some cases, the implant insertion device or the implant body is made of at least one durable material. In some cases, the implant body is made of one or more durable materials so that the implant body functionally last for at least one year, 1.5 year, or 2 years. In some cases, the implant insertion device or the implant body is made of at least one material that is compatible with one or more medical imaging modalities. In some cases, the one or more medical imaging modalities includes: MRI, X-ray, CT, PET, SPECT, and ultrasound. In some cases, the inner shaft body and the inner shaft tip is made of at least one metal. In some cases, the at least one metal increases reduces unwanted breakage of the inner shaft during implant insertion.

In some embodiments, the implant body is made of at least one selected from: polyether ether ketone (PEEK), carbon fiber-reinforced polymer, carbon fiber-reinforced plastic, carbon fiber-reinforced thermoplastic, glass fiber-reinforced polymer, glass fiber-reinforced plastic, and polyaryletherketone (PEAK).

In some embodiments, the inner shaft, the outer shaft, or the inner shaft and the outer shaft is made of one selected from: at least one selected from carbon fiber-reinforced polymer, carbon fiber-reinforced plastic, carbon fiber-reinforced thermoplastic, glass fiber-reinforced polymer, glass fiber-reinforced plastic, Ixef, and polyarylamide (PARA), or any commercially available polymer of a similar nature. In some cases, the inner shaft or the outer shaft comprises about 50% glass in its material. In some cases, the inner shaft or the outer shaft comprises a material having a glass content of at least 10% to no greater than 70%. In other cases, the inner shaft or the outer shaft includes a material having a glass content of at least one selected from 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%.

In some cases, the implant is made of titanium. In some cases, the inner shaft body, the inner shaft, or the outer shaft is made of nitinol, stainless steel, titanium, or other similar metals.

In some embodiments, the inner shaft is made of a flexible material such as a material that maintains integrity if bent laterally. In some cases, the inner shaft is flexible such that it can be threaded into a curved outer shaft.

Implant devices and systems as disclosed herein are used to deliver graft material to a number of patient locations. Exemplary locations include intervertebral spaces, such as lumbar intervertebral spaces, cervical intervertebral spaces, or other intervertebral spinal spaces. In some cases, the devices and methods disclosed herein are used to deliver a graft or inert to a non-vertebral space of a patient, such as a bone exterior or interior, or a soft tissue.

Sizes:

In some cases, the implant body is properly sized in three spatial dimensions so that it fits into an intervertebral space that needs to be inserted. In some cases, the implant body is properly is sized to endure the force, pressure, or worn after insertion for a pre-determined period of time.

In some cases, when the height, length, or width is not uniform, the height, length, and width here indicate the minimal height, length, or width. In other cases, when the height, length, or width is not uniform, the height, length, and width here indicate the average height, length, or width.

In some embodiments, the implant body has a height of no less than 1 mm and no more than 3 cm. In some cases, the height of the implant body is in the head-to-toe direction when it is properly inserted. In some cases, the implant body has a width of no less than 5 mm and no more than 8 cm. In some cases, the width of the implant body is in the left-to-right direction when it is properly inserted. In some cases, the implant body has a length of no less than 5 mm and no more than 8 cm. In some cases, the length of the implant body is in the anterior-to-posterior direction, when it is properly inserted. In some cases, the internal space has a height of no less than 1 mm and no more than 3 cm. In some cases, the height of the internal space is in the head-to-toe direction when it is properly inserted. In some cases, the internal space has a width of no less than 5 mm and no more than 8 cm. In some cases, the width of the internal space is in the left-to-right direction when it is properly inserted. In some cases, the internal space has a length of no less than 5 mm and no more than 8 cm. In some cases, the length of the internal space is in the anterior-to-posterior direction, when it is properly inserted. In some cases, the wall thickness of the supporting structure is no less than 1 mm and no more than 3 cm.

In some embodiments, the main slot of the implant body has a height of no less than 2 mm and no greater than 5 cm. In some cases, the main slot has a width and a length of no less than 2 mm and no greater than 5 cm. In some cases, the main slot has a height, width or length of one selected from: 1 mm, 1.5 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 10 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, or 45 mm.

In some cases, the chamber of the implant body has a U shape. In some cases, the bottom part of the U shape is a half circle. In some cases, the diameter of the half circle is the length or width of the chamber. In some cases, the diameter is one selected from: 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 10 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, and 50 mm.

In some cases, the depth of the chamber, i.e., the indented depth from the edge of the main slot to the opposite side of the chamber, is slighter greater than the depth of the inner shaft tip so that it allows the inner shaft tip to be fully enclosed in the chamber and rotate therewithin. The depth of the chamber is no less than 1 mm to no greater than 2 cm. In some cases, the depth of the chamber or the inner shaft tip is selected from 1 mm, 1.2 mm, 1.5 mm, 1.8 mm, 2 mm, 2.2 mm, 2.5 mm, 2.8 mm, 3 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 10 mm, 21 mm, 22 mm, 23 mm, 24 mm, and 25 mm. In some cases, the depth of the inner shaft tip is perpendicular to the rotation plane of the inner shaft.

In some cases, each side slot has an arbitrary three-dimensional shape. In some cases, each side slot has a three dimensional volume smaller than the main slot. In some cases, each of the outer shaft tips has an arbitrary three dimensional shape that fit in a matching side slot.

In some cases, the inner shaft tip has a shape that is substantially similar and slightly smaller than the main slot so that it can pass through the main slot by keeping the main axis of the inner shaft tip and the main axis of the main slot substantially parallel.

In some cases, the inner shaft body has a length or a size of the longest dimension selected from about 4.5 inches, about 5 inches, about 5.5 inches, about 6 inches, about 6.5 inches, about 7 inches, about 7.5 inches, about 8 inches, about 8.5 inches, about 9 inches, about 9.5 inches about 10 inches, about 10.5 inches, about 11 inches, about 11.5 inches, about 12 inches, or about 12.5 inches. In some cases, the outer shaft has a length or a size of the longest dimension of one selected from about 4.5 inches, about 5 inches, about 5.5 inches, about 6 inches, about 6.5 inches, about 7 inches, about 7.5 inches, about 8 inches, about 8.5 inches, about 9 inches, about 9.5 inches about 10 inches, about 10.5 inches, about 11 inches, about 11.5 inches, about 12 inches, or about 12.5 inches. In some cases, the implant insertion device has a longest dimension selected from about 4.5 inches, about 5 inches, about 5.5 inches, about 6 inches, about 6.5 inches, about 7 inches, about 7.5 inches, about 8 inches, about 8.5 inches, about 9 inches, about 9.5 inches about 10 inches, about 10.5 inches, about 11 inches, about 11.5 inches, about 12 inches, or about 12.5 inches.

In some embodiments, the cross section along the longest dimension of the outer shaft monotonically decreases from the base to the insertion end of the insertion device. The greatest cross section of the implant insertion device or the outer shaft, i.e., the bottom-most cross section, perpendicular to the longest dimension of the outer shaft has a width or a length of no less than 5 mm and no greater than 8 cm. The top-most cross section of the inner shaft body or the outer shaft has a width or a length of no less than 2 mm and no greater than 2 cm.

In some embodiments, part of the knob of the inner shaft fits into the outer shaft. In some cases, part of the knob does not fit into the outer shaft. The at least one hump fits into the outer shaft. The size of the hump has an area of no less than 1 mm cm$^2$ and no greater than 1 cm$^2$.

In some embodiments, the outer face of the outer shaft is a flat two dimensional surface. In other cases, the outer face is a concave surface or a convex surface. In some cases, the outer face includes a circular opening. In other cases, the outer face includes an arbitrary two dimensional shape opening that allows passage of the inner shaft tip.

In some cases, the inner shaft comprises a cam feature at the base of the inner shaft. In some cases, the cam feature has a height of no less than 0.2 mm and no greater than 1 cm. In some cases, the insertion stopper has a height of no less than 0.2 mm and no greater than 2 cm.

Graft tissue, as used herein, may comprise autologous patient tissue, such as bone tissue taken from elsewhere in the patient during the procedure. Graft tissue may also be cadaverous, or may be cultured or synthetically produced from cultured differentiated or undifferentiated cell populations derived from the patient or elsewhere. Grafting material may be packed allograft bone (demineralized or not), packed biocompatible ceramics granules (beta-tricalcium phosphate, hydroxyapatite, calcium sulfate, and equivalents) to assume the graft volume shape, biocompatible ceramic granules held by biocompatible matrix such as collagen with or without bioglass and with or without hyaluronic acid.

Insertion bodies, i.e., implant bodies, as disclosed herein, are used to deliver graft tissue to an intervertebral space of a patient in some case. Insertion bodies may also be used in the absence of graft tissue, such as to deliver an artificial structure to the internal space of a patient. In some cases an insertion device is used to deliver an insert to the interior of a patient that is distinct from the spine, such as a joint, bone graft location, or bone reconstruction location. In some cases an insertion device delivers an insert that does not comprise an internal space, or that is configured for a use other than to stabilize a graft between two vertebrae. Accordingly, both spinal interventions and non-spinal interventions are contemplated herein, and implant bodies consistent with the respective intervention are similarly contemplated.

Cylindrical Shapes:

In some embodiments, the claimed devices, methods, or kits involve a cylindrical shape, a substantially cylindrical shape or use of the same. In some cases, a cylindrical shape is a three-dimensional (3D) shape. In some cases, a cylindrical shape has a cross section of an arbitrary two-dimensional (2D) shape formed by a closed contour, and the cylindrical shape is formed by a stack of a finite number of cross sections of the same arbitrary two dimensional shape placed adjacent to each other.

In some cases, a cylindrical shape has a cross section of a trapezoid formed by a closed contour, and the cylindrical shape is formed by a stack of identical trapezoids placed adjacent to each other. In some cases, a cylindrical shape has an elliptical cross section formed by a closed contour, and the cylindrical shape is formed by a stack of identical ellipses placed adjacent to each other. In some cases, a cylindrical shape has a rectangular cross section formed by a closed contour, and the cylindrical shape is formed by a stack of identical rectangles placed adjacent to each other.

In some embodiments, a cylindrical shape is a group of parallel lines placed continuously adjacent to each other. In some cases, this group of parallel lines is of a uniform height. In other embodiment, these parallel lines are of different height.

In some cylindrical shapes, all parallel cross sections are of equal area, while in other embodiments, parallel cross sections vary in surface area, for example, by monotonically increasing or decreasing in a 'tapered cylindrical shape'.

Rectangular Cuboid:

In some embodiments, the claimed devices, methods, or kits involve a rectangular cuboid, a cuboid, or use of the same. In some cases, a rectangular cuboid is a three dimensional shape. In some cases, a rectangular cuboid has a cross section of a two dimensional rectangle formed by a closed contour, and a rectangular cuboid is formed by a stack of a finite number of cross sections of the same two dimensional rectangle shape placed adjacent to each other. Similarly, in some cases, a cuboid has a cross section of a two dimensional rectangle formed by a closed contour, and a cuboid is formed by a stack of a finite number of cross sections of the same two dimensional rectangle shape placed adjacent to each other.

Cylindrically Elliptical:

In some cases, a cylindrically elliptical shape has a cross section of an ellipse formed by a closed contour, and the cylindrically elliptical shape is formed by a stack of identical ellipses placed adjacent to each other.

Internal Spaces:

In some embodiments, the internal space of the implant body is partly enclosed by the implant body in three dimensional space. In some cases, the internal space is not covered in its top-most cross section. In some cases, the internal space is not covered in its bottom-most cross section. In some cases, the internal space is not covered in its top-most cross section and bottom-most cross section. In some cases, the internal space is not covered in its top and bottom faces. In some cases, the internal space is a three dimensional hole throughout one dimension of the support structure. In some cases, the internal space is a three dimensional hole throughout one dimension of the support structure and covered by a wall of the support structure in other directions.

Slots:

In some embodiments, an implant body has a main slot indented into a wall of the implant body. In some cases, the inner shaft tip fits through a main slot when a major axis of the main slot and a major axis of the inner shaft tip are substantially parallel. In some cases, substantially parallel includes an acute intersecting angle of the major axis of the main slot and the major axis of the inner shaft tip, wherein the intersecting angle less than 10 degrees. In some cases, substantially parallel includes an acute intersecting angle of the major axis of the main slot and the major axis of the inner shaft tip, wherein the intersecting angle less than 5 degrees. In some cases, substantially parallel includes an acute intersecting angle of the major axis of the main slot and the major axis of the inner shaft tip, wherein the angle less than 15 degrees. In some cases, the inner shaft tip fits through a main slot when the inner shaft is rotated to a second position and the top or bottom-most outer surface of the implant body is substantially parallel to the major axis of the main slot. In some cases, the inner shaft tip fits through a main slot when the inner shaft is rotated to a second position and the top or bottom-most outer surface of the implant body is substantially parallel to the major axis of a cross section of the main slot. In some cases, the cross section is substantially perpendicular to the top or bottom-most outer surface of the implant body.

In some embodiments, a slot is a two dimensional shape with a close contour with a negligible size in the third dimension. In some cases, a negligible size is at least 10 times smaller than any other two dimensions. In other cases, a negligible size is at least 50 times smaller than any other two dimensions. In other cases, a negligible size is at least 100 times smaller than any other two dimensions. In other cases, a negligible size is at least 200 times smaller than any other two dimensions.

In some embodiments, the main slot of the implant body allows rotation of the inner shaft tip therewithin. In some cases, the main slot allows rotation of the inner shaft tip therewithin through at least 60 degrees. In some cases, the main slot allows rotation of the inner shaft tip therewithin through at least 70 degrees. In some cases, the main slot allows rotation of the inner shaft tip therewithin through at least 80 degrees. In some cases, the main slot allows rotation of the inner shaft tip therewithin through at least 90 degrees. In some cases, the main slot allows rotation of the inner shaft tip therewithin so that the inner shaft tip is locked to the implant body. In some cases, the main slot allows rotation of the inner shaft tip therewithin so that the inner shaft is locked to the implant body. In some cases, the main slot allows rotation of the inner shaft tip therewithin in a manner such that the implant body is locked to the inner shaft. In some cases, the main slot allows rotation of the inner shaft tip therewithin in a manner such that the implant body is not separable from the inner shaft by any linear movement.

In some embodiments, a main slot of the implant body is a cylindrical shape. In some cases, a cross section of the main slot is an ellipse. In some cases, a cross section of the main slot is a rectangle. In some cases, a cross section of the main slot is a rhombus shape. In some cases, a cross section of the main slot is a triangle. In some cases, the cross section of the main slot is a parallelogram.

In some embodiments, a main slot of the implant body is indented from an outer surface of the implant body. In some cases, a main slot is indented from an outer surface towards an inner surface of the implant body in a direction that is parallel to the proper implant insertion direction. In some cases, the bottom cross section of the main slot is on the outer surface of the implant body.

In some embodiments, an implant body has two side slots indented into a wall of the implant body. In some cases, an implant body has two side slots indented into the same wall of the main slot of the implant body. In some cases, two side slots are indented from an outer surface of the implant body. In some cases, two side slots are indented from an outer surface towards an inner surface of the implant body in a direction that is parallel to the proper implant insertion direction. In some cases, the bottom cross sections of two side slots are on the outer surface of the implant body. In some cases, the bottom cross sections of two side slots are symmetrically adjacent to the bottom cross section of the main slot. In some cases, the bottom cross sections of two side slots are symmetric with respect to the mid-point or center of the bottom cross section of the main slot. In some cases, the bottom cross sections of two side slots are symmetric with respect to the minor axis of the bottom cross section of the main slot. In some cases, the bottom cross sections of two side slots are symmetric with respect to the major axis of the bottom cross section of the main slot. In some cases, the bottom cross sections of two side slots are symmetric with respect to the longest axis of the bottom cross section of the main slot. In some cases, the bottom cross sections of two side slots are symmetric with respect to a diagonal of the bottom cross section of the main slot. In some cases, the bottom cross sections of two side slots are symmetric with respect to the width of the bottom cross section of the main slot. In some cases, each of the two side slots fits to one of the two outer shaft tips when the implant body is properly locked to the outer shaft. In some cases, the fitting of each of the two side slots to one of the two outer shaft tips when the implant body the implant body is properly locked to the outer shaft is configured to hold the implant body against the implant insertion device. In some cases, the properly locking of the implant body to the outer shaft is configured to attach the side slots to the tips. In some cases, the properly attachment of the implant body to the outer shaft prevent the implant body from accidental rotation during implant insertion. In some cases, the properly attachment of the implant body to the outer shaft prevent the implant body from accidental rotation around the inner shaft body during implant insertion. In some cases, the properly attachment of the implant body to the outer shaft prevent the implant body from accidental rotation around the direction of insertion during implant insertion. In some cases, the proper locking of the implant body to the outer shaft is configured to facilitate reduction of pressure on the implant body during insertion. In some cases, the proper locking of the implant body to the outer shaft is configured to reduce unwanted implant release from the implant insertion device during insertion. In some cases, the proper locking of the implant body to the outer shaft is configured to increase the area of interaction between the implant body and the implant insertion device. In some cases, the proper locking of the implant body to the outer shaft is configured to increase the area of interaction with the implant body so that the force on the implant body is partly transferred to the implant insertion device. In some cases, the proper locking of the implant body to the outer shaft is configured to decrease the risk of implant breakage. In some cases, the proper locking of the implant body to the outer shaft is configured to decrease the risk of unwanted implant detachment from the implant insertion device. In some cases, proper locking holds the implant body in place such that it can be more accurately placed into an intervertebral space of a patient.

In some embodiments, two side slots are each of a semi-cylindrical shape. In some cases, a cross section of each of the two side slots is a semi-ellipse. In some cases, a cross section of each of the two side slots is a rectangle. In some cases, a cross section of each of the two side slots is a semi-rectangle. In some cases, a cross section of each of the two side slots is a triangle. In some cases, a cross section of each of the two side slots is a circle sector. In some cases, a cross section of each of the two side slots is a circle. In some cases, a cross section of each of the two side slots is a trapezoid. In some cases, a cross section of each of the two side slots is a pentagon or a rhombus. In some cases, the cross section of each of the two side slots is a parallelogram. In some cases, a cross section of each of the two side slots is an arbitrary two dimensional shape.

In some cases, the implant body includes a slot at the top or the bottom cross section of the implant body. In some cases, the slot is indented from a top-most region or a bottom-most region of the outer surface along the longitudinal direction. In some cases, this slot is connected to the chamber of the implant body. In some cases, this slot facilitates the molding of the chamber. In some cases, the slot enables visualization of the inner shaft tip within the chamber. In some embodiments, the slot has a width substantially identical to the width of the chamber. In other embodiments, the slot has a width substantially identical to the diameter of the chamber.

In some embodiments, the main slot faces anterior, posterior, left, right, head, or toe side of the patient when the implant body is properly deployed in the patient. In some embodiments, the main slot is located on any face of the support structure. In some cases, the presence of the slot does not affect the locking of the implant body to the insertion device.

Figure 6:
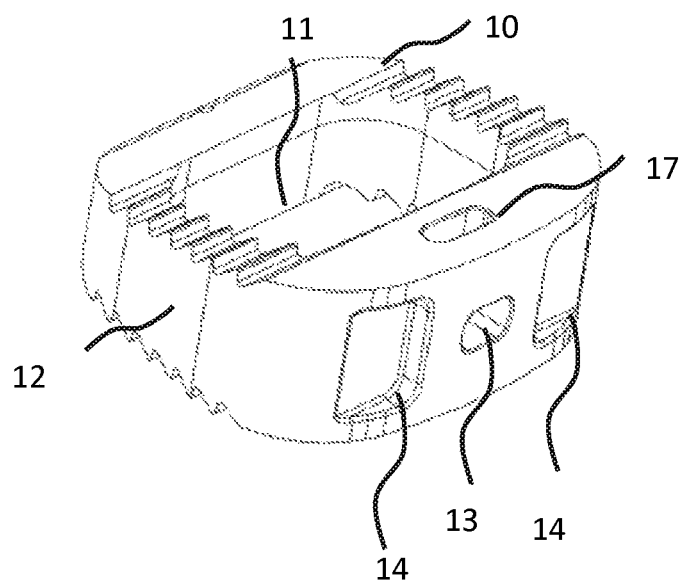
FIG. 6 shows an embodiment of the implant body.

Referring to FIG. 6, in a particular embodiment, an implant body is shown. The implant body 10 has a support structure 12 that encloses an internal space 11 that can be filled by graft materials. The implant body has a main slot 13 indented from the side of the support structure. Two side slots 14 are symmetrically located proximal to the main slot 13 on the side wall of the implant body 10. A top slot 17 connects to the chamber that is accessible from the main slot 13. In some embodiments, the size of side slots 14 is smaller than the main slot 13. In some embodiments, each side slot 314 is optional. In some embodiments, the main slot is threaded to fit a threaded inner shaft tip therewithin by threading.

Supporting Structures:

In some embodiments, the implant body contains a supporting structure. In some embodiments, the supporting structure is made of at least one injection moldable material. In some embodiments, a supporting structure is equivalent to an implant body. In some embodiments, the implant body comprises a supporting structure, an internal space for holding at least one graft material, and at least one space for holding at least one medical imaging tag. In some embodiments, the at least one space for holding at least one medical imaging tag is in an edge of the supporting structure. In some embodiments, the at least one space for holding at least one medical imaging tag is located to facilitate the recognition of the implant body with at least one medical imaging modalities. In some embodiments, the at least one medical imaging modality includes one or more selected from: MRI, CT, X-ray, PET, microPET, micro-SPECT, OCT, and ultrasound.

Chambers:

In some embodiments, the implant body includes a chamber. In some embodiments, a chamber is sized so that an inner shaft tip can rotate within a chamber to assume at least two positions. In some embodiments, the first position in the chamber is a locked position so that the inner shaft tip cannot be withdrawn from the chamber without a rotation of the inner shaft tip in the coronal or sagittal plane to a second position. In some embodiments, the second position in the chamber is an unlocked position so that the inner shaft tip can be withdrawn from the chamber only with linear movement of the inner shaft tip. In some embodiments, the linear movement is along the insertion direction toward the base of the implant insertion device.

In some embodiments, the implant body only accesses the chamber via movement through the main slot. In some cases, the chamber is indented deeper in the wall of the implant body than the main slot. In some embodiments, the chamber is connected to at least one slot. In some cases, the chamber is connected to at least one opening in the supporting structure of the implant body.

Major Axis:

In some embodiments, a major axis is the longest diameter of a two dimensional ellipse. In some embodiments, the major axis is the longest diameter of a cross section of a cylindrical shape, wherein the cross section is parallel to the base or top of the cylindrical shape. In some embodiments, the major axis of a rectangle is the length of the rectangle. In some embodiments, the major axis of a cuboid is the longest diameter of a cross section of the cuboid, wherein the cross section is parallel to the base or top of the cuboid. In some embodiments, the major axis of a rectangular cuboid is the longest diameter of a cross section of the rectangular cuboid, wherein the cross section is parallel to the base or top of the cuboid.

In some embodiments, the major axis of the main slot and the major axis of the inner shaft tip are not substantially parallel if an acute angle of greater than 9 degrees is formed between the major axis of the main slot and the major axis of the inner shaft tip. In some embodiments, the major axis of the main slot and the major axis of the inner shaft tip are not substantially parallel if an acute angle of greater than 4 degrees is formed between the major axis of the main slot and the major axis of the inner shaft tip. In some embodiments, the major axis of the main slot and the major axis of the inner shaft tip are not substantially parallel if an acute angle of greater than 7 degrees is formed between the major axis of the main slot and the major axis of the inner shaft tip. In some embodiments, the major axis of the main slot and the major axis of the inner shaft tip are not substantially parallel if an acute angle of greater than 14 degrees is formed between the major axis of the main slot and the major axis of the inner shaft tip.

In some embodiments, the major axis of the main slot and the major axis of the inner shaft tip are not substantially parallel if an angle of about 90 degrees is formed. In some embodiments, the major axis of the main slot and the major axis of the inner shaft tip are not substantially parallel if an acute angle of at least 15 degrees is formed in between the two major axes.

Cross Sections:

In some embodiments, a cross section is the intersection of a three dimensional body with a plane. In some embodiments, the cross section is parallel to the base or top of the three dimensional body. In some embodiments, a cross section is the intersection of a three dimensional body with a plane that is parallel to the base or top of the three dimensional body. In some embodiments, a cross section of three dimensional body includes a contour.

Inner Shaft Tips:

In some cases, the claimed devices, methods, or kits involve an inner shaft tip or user of the same. In some embodiments, the inner shaft tip is attached to the inner shaft body at the insertion end of an inner shaft. In some embodiments, the inner shaft tip contacts the implant body. In some embodiments, the inner shaft tip fits in the main slot of the implant body. In some embodiments, the inner shaft tip fits in the main slot of the implant body when a major axis of the inner shaft tip is substantially parallel to a major axis of the main slot of the implant body. In some embodiments, substantially parallel includes an acute intersecting angle of less than 10 degrees. In some cases, substantially parallel includes an acute intersecting angle of less than 5 degrees. In some embodiments, substantially parallel includes an acute intersecting angle of less than 15 degrees.

In some embodiments, the inner shaft tip rotates in the main slot of the implant body to lock the implant body to the inner shaft. In some embodiments, the inner shaft tip is cylindrical. In some embodiments, the cross section of the inner shaft tip is elliptical. In some embodiments, the cross section of the inner shaft tip is rectangular. In some embodiments, the cross section of the inner shaft tip is rhombus. In some embodiments, a cross section of the inner shaft tip is a triangle. In some embodiments, the cross section of the inner shaft tip is a parallelogram.

In some cases, the inner shaft tip is attached to the inner shaft body on it bottom-most cross section. In some cases, the bottom-most cross section of the inner shaft tip is attached to the top-most cross section of the inner shaft body. In some cases, the bottom-most cross section is elliptical. In some embodiments, the mid-point of the major axis of the bottom-most cross section of the inner shaft tip overlaps with the center of the top-most cross section of the inner shaft body. In some cases, the inner shaft tip rotates concentrically when the inner shaft body rates within an outer shaft.

In some embodiments, the inner shaft tip is not enclosed in the outer shaft, when the inner shaft is properly deployed. In some embodiments, the inner shaft body is substantially enclosed in the out shaft when the inner shaft is properly deployed. In some embodiments, substantially enclosed indicates that at least 95% of the volume of the inner shaft body is enclose. In some embodiments, substantially enclosed includes at least 98% of the volume of the inner shaft body is enclosed by the outer shaft. In some embodiments, substantially enclosed includes at least 99% of the volume of the inner shaft body is enclosed by the outer shaft. In some embodiments, substantially enclosed includes at least 92% of the volume of the inner shaft body is enclosed by the outer shaft.

Figure 7:
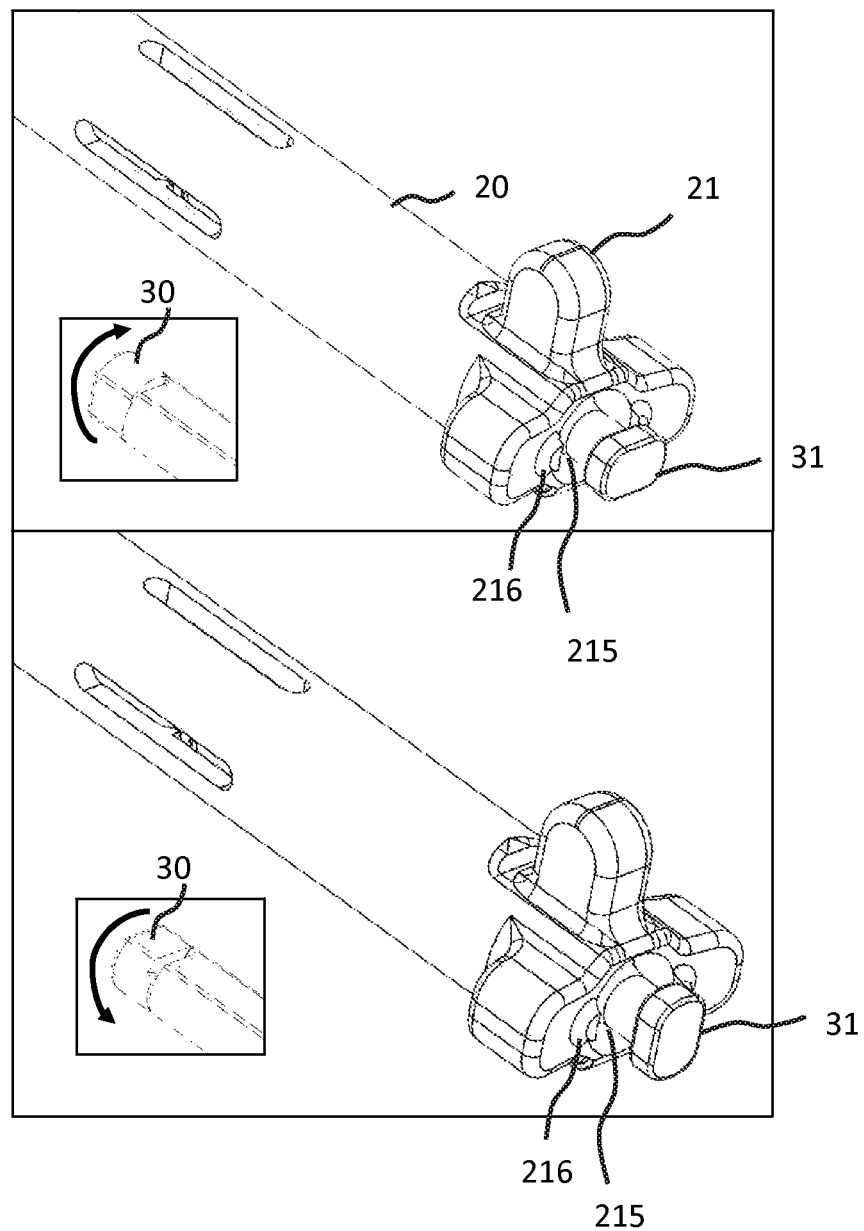
FIG. 7 shows the embodiment of the inner shaft and outer shaft of the implant insertion device in FIG. 2.

Referring to FIG. 7, in a particular case, mechanism of locking an implant body to the inner shaft and outer shaft is shown. In this embodiment, the inner shaft is properly inserted in the outer shaft 20. The inner shaft tip 31 fit through the outer shaft opening 215. The knob of the inner shaft 30 is turnable at the base of the implant insertion device to rotate the inner shaft tip 31 for about 90 degrees. The outer shaft tips 216 are symmetrically located by the outer shaft opening and are configured to attach to the two side slots of an implant body. The inner shaft tip is substantially cylindrical ellipse. When the elliptical cross section substantially aligns with the elliptical cross section of an implant body (top image), the implant body is readily loaded to the inner shaft tip 31. When the elliptical cross section rotates about 90 degrees from the elliptical cross section of an implant body (bottom image), the implant body is locked to the inner shaft tip 31. The implant body is further attached to the outer shaft via attachment to the outer shaft tips 22 symmetrically located proximal to the outer shaft opening 215. In some embodiments, the insertion stopper 21 is optional. In some embodiments, the insertion stopper 21 is only present at certain operating angle of the implant insertion system. In some embodiments, the outer shaft opening 215 is circular. In some embodiments, the outer shaft opening 215 is a two dimensional area that big enough to allows inner shaft tip 31 to pass through from the base toward the insertion end of the outer shaft.

Figure 8:
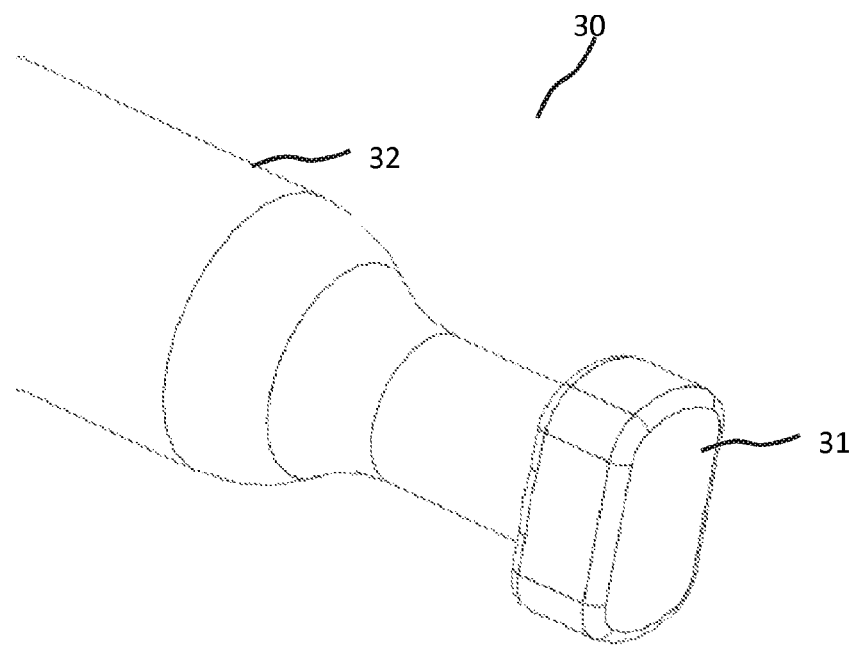
FIG. 8 shows an embodiment of the inner shaft tip.

Referring to FIG. 8, in particular embodiments, an inner shaft 30 is shown with a rod-shaped inner shaft body 32 and a substantially cylindrically elliptical shaped inner shaft tip 31 wider than the part that the tip is immediately adjacent to. In some cases, the inner shaft tip 31 is cylindrical cuboid. In some cases, the inner shaft tip is a cube. In some embodiments, the inner shaft tip is a cylindrical triangle. In some embodiments, the inner shaft tip is cylindrical parallelogram. In some embodiments, the inner shaft tip is cylindrical trapezoid. In some embodiments, the inner shaft tip is an arbitrary three-dimensional shape except a cylinder or a sphere. In some embodiments, the inner shaft tip 31 is wider than the inner shaft body immediately adjacent thereto in at least one dimension perpendicular to a plane of rotation of the inner shaft tip. In some embodiments, the inner shaft body 32 is flexible so as to fit in a curved or bent outer shaft and rotate therewithin.

Knobs:

In some embodiments, the knob is not enclosed in the outer shaft, when the inner shaft is properly deployed. In some embodiments, the knob is attached to the base of the inner shaft body. In some embodiments, the knob is attached to the inner shaft body on it top-most cross section. In some embodiments, the top-most cross section of the inner shaft tip is attached to the bottom-most cross section of the inner shaft body at the base of the inner shaft body. In some embodiments, the knob of the inner shaft includes a knob that is attached to the base of the inner shaft body. In some embodiments, the knob is attached to the bottom-most cross section of the inner shaft body. In some embodiments, the knob has a larger cross sectional area than the cross sectional area of the bottom-most cross section of the inner shaft body. In some embodiments, the center of the knob and the center of the bottom-most cross section of the inner shaft body are aligned along the longest axis of the inner shaft. In some embodiments, the top-most cross section is substantially square. In some embodiments, the top-most cross section is substantially elliptical. In some embodiments, the center of the top-most cross section of the knob overlaps with the center of the bottom-most cross section of the inner shaft body. In some embodiments, the inner shaft body rotates concentrically within an outer shaft when the knob rotates. In some embodiments, the top cross sectional area of the knob is substantially the same or bigger than the bottom-most cross-sectional area of the outer shaft. In some embodiments, the knob is not inserted into the outer shaft when the inner shaft is properly deployed. In some embodiments, the knob is not enclosed by the outer shaft when the inner shaft is properly deployed.

Interfaces:

In some embodiments, the implant insertion device and implant body includes at least one, two, three, or more than three interfaces. In some embodiments, the implant insertion device and implant body includes at least one, two, or three complimentary interfaces.

In some embodiments, an interface and a complementary interface are elements or structures performing complementary functions to each other. In some embodiments, an interface comprises an equivalent structure to at least one outer shaft tips or at least one side slot. In some cases, an interface comprises an equivalent structure to a cam feature or two different surfaces that a cam feature can slide thereon. In certain embodiments, the two different surfaces are displaced by a predetermined distance. In certain embodiments, the predetermined distance is the maximal distance that the inner shaft tip can move in one direction with respect to the outer shaft.

In some embodiments, a complementary interface is an equivalent structure to at least one outer shaft tip or at least one side slot. In some cases, a complementary interface is an equivalent structure to a cam feature or two different surfaces that a cam feature can slide thereon. In certain cases, the two different surfaces are displaced by a predetermined distance. In certain embodiments, the predetermined distance is the maximal distance that the inner shaft tip can move in one direction with respect to the outer shaft when the inner shaft is rotated to lock the implant body in place.

In some embodiments, an interface comprises at least one tip. In some embodiments, an interface comprises at least one slot to fit a tip. In some embodiments, an interface comprises at least a cam feature. In some embodiments, an interface comprises two different surfaces that a cam feature can slide on. In certain embodiments, the two different surfaces are displaced by a predetermined distance. In some embodiments, the predetermined distance is the maximal distance that the inner shaft tip can move in one direction with respect to the outer shaft.

In some embodiments, a complimentary interface is at least one tip. In some embodiments, a complimentary interface is at least one slot to fit a tip. In some embodiments, a complimentary interface is at least a cam feature. In some embodiments, a complimentary interface is two different surfaces that a cam feature can slide on. In certain embodiments, the two different surfaces are displaced by a predetermined distance. In some embodiments, the predetermined distance is the maximal distance that the inner shaft tip can move in one direction with respect to the outer shaft.

In some embodiments, the first or the second interface comprises a cam feature. In some cases, the first or the second interface comprises two different surfaces that a cam feature can slide on. In some cases, the first or the second interface comprises at least two tips. In some embodiments, the first or the second interface comprises at least two slots to fit the at least two tips individually.

In some embodiments, the first or the second complimentary interface comprises a cam feature. In some embodiments, the first or the second complimentary interface comprises two different surfaces that a cam feature can slide on. In some embodiments, the first or the second complimentary interface comprises at least two tips. In some embodiments, the first or the second complimentary interface comprises at least two slots to fit the at least two tips individually.

In certain embodiments, the first interface comprises a cam feature. In some embodiments, the cam feature is attached to a knob of an inner shaft. In other embodiments, the cam feature is attached to an outer shaft. In some embodiments, the first complimentary interface comprises two different surfaces connected by a ramp feature that the cam feature can slide on. In some embodiments, the two different surfaces are at the outer shaft. In some embodiments, the two different surfaces are at the knob. In some embodiments, the second interface comprises at least two spatially separated slots. In some embodiments, the at least two spatially separated slots are in the implant body. In other embodiments, the at least two spatially separated slots are in the outer shaft. In some embodiments, the second complimentary interface comprises at least two spatially separated tips that fits in the at least two spatially separated slots. In some embodiments, the at least two spatially separated tips are on the outer shaft. In some embodiments, the at least two spatially separated tips are on the implant body.

In some embodiments, the first interface is a cam feature or two different surfaces that a cam feature can slide on. In some embodiments, the first complementary interface is a cam feature or two different surfaces that a cam feature can slide on. In some embodiments, the second interface is a slot or a tip that fits to the slot. In some embodiments, the second complementary interface is a slot or a tip that fits to the slot. In some embodiments, the second interface is a side slot or an outer shaft tip that fits to the side slot. In some embodiments, the second complimentary interface is a side slot or an outer shaft tip that fits to the side slot.

In some embodiments, the first interface, the second interface, the first complimentary interface, and the second complimentary interface are each selected from the list of: a cam feature, two different surfaces that the cam feature slides on, a slot, and a tip that fits to the slot.

In some embodiments, the third interface is a hump. In some embodiments, the third complimentary interface is a hump. In some embodiments, the third interface is at the knob. In some embodiments, the third interface is at the inner surface of the outer shaft. In other embodiments, the third complementary interface is at the knob. In some embodiments, the third complementary interface is at the inner surface of the outer shaft.

In some embodiments, the third interface unlocks the hump at the first position and locks the hump at the second position. In some embodiments, the third interface is a window indented from the outer surface through the inner surface. In some embodiments, the third interface further includes a groove at the first position configured to allow the inner shaft to be pulled out from the base of the outer shaft. In some embodiments, the groove started from the base of the outer shaft and goes along the outer shaft until it connects with the window of the outer shaft.

In some embodiments, the hump is inserted into the outer shaft when it is locked at the second position. In some embodiments, the hump is visible through the window of the outer shaft at least at the locked position. In other embodiments, the hump is visible through the window of the outer shaft at the locked and the unlocked position. The hump is at least 5 mms and no greater than 5 cm away from the base of the outer shaft toward the insertion end of the insertion device.

In some embodiments, the outer shaft and the inner shaft interact via an interface and a complementary interface to lock or unlock to each other. In some cases, the interface or the complementary interface comprises a camp or two displaced surfaces that the cam is configured to access so as to generate a linear displacement between the outer shaft and the inner shaft. In some cases, the two displaced surfaces are connected by a ramp. In some cases, the two displaced surfaces are connected by a step. In some embodiments, the two displaced surfaces are connected by a curve, a groove, a notch, a dent, or a hump. In some embodiments, the two displaced surfaces are connected by at least one stair. In some embodiments, switching between the two displaced surfaces are configurable with the assistance of actuation elements including one or more of: a gear, a gear set, a latch, a bolt, a threaded fitting, a clip, a magnetic element, a clamp, a hook, a spring, or a switch.

In some embodiments, the inner shaft and the implant body interacts via an interface and a complementary interface to lock or unlock one to the other. In some embodiments, the interface or the complementary interface comprises a slot and a tip that can fit through the slot and rotate in order to lock or unlock one to each other. In some embodiments, the interface or the complementary interface comprises threaded and fitted elements. In some embodiments, the interface or the complementary interface comprises a latching and a latchable element. In some embodiments, the interface or the interface comprises threaded and fitted elements. In some embodiments, the interface or the complementary interface comprises a clipping and a clipable element. In some embodiments, the interface or the complementary interface comprises gearing elements. In some embodiments, the interface or the complementary interface comprises magnetic elements.

Figure 9:
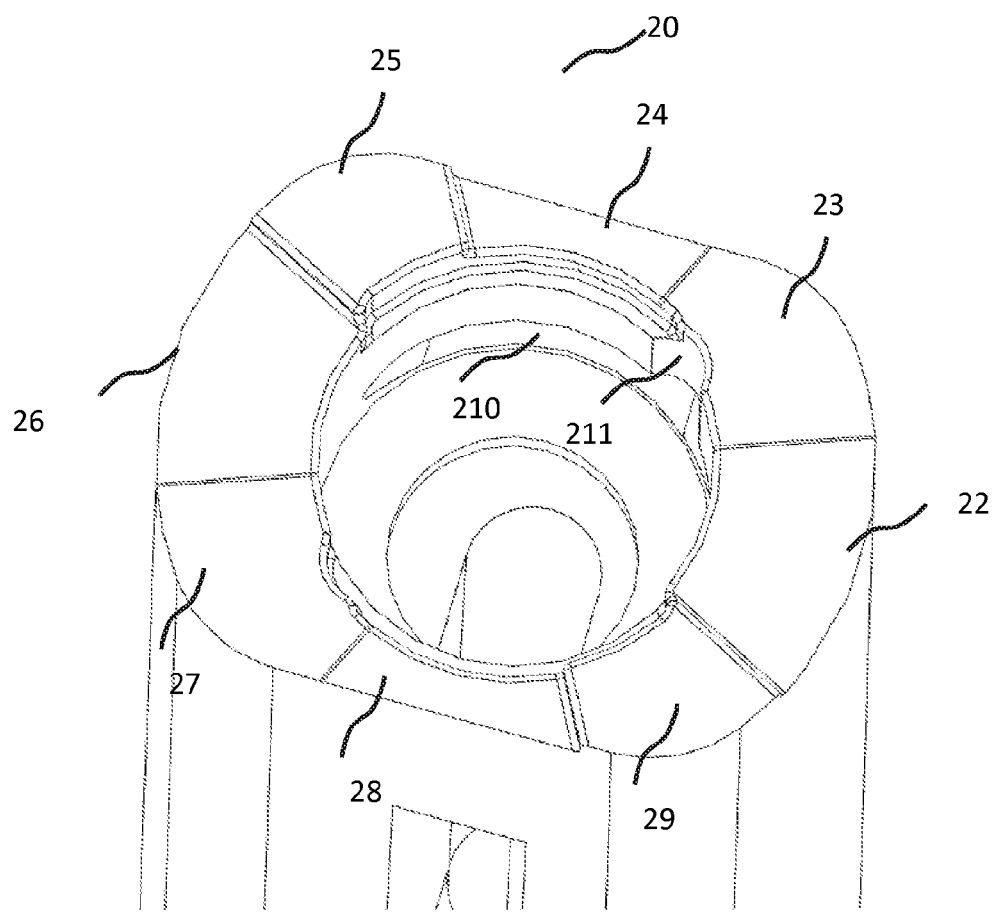
FIG. 9 shows an embodiment of the base of the outer shaft.

Referring to FIG. 9, in a particular embodiment, the outer shaft 20 includes a groove 211 at the inner surface of the outer shaft that a hump of the knob can slide along. The outer shaft also has a window 210 indented from the outer surface to the inner surface of the outer shaft. The edge of the window connects with the groove so that the hump can slide along the groove 211 into the window 210. At the first position, the hump is aligned with the groove 211 and the window 210 edge connecting to the groove 211. When the inner shaft rotates about 90 degrees to the second position, the hump is at the opposite edge of the window 210. In some embodiments, the window 210 and the hump that can be locked or unlocked to the window 210 is replaceable by an interface and a complementary interface that are functionally equivalent.

Figure 10:
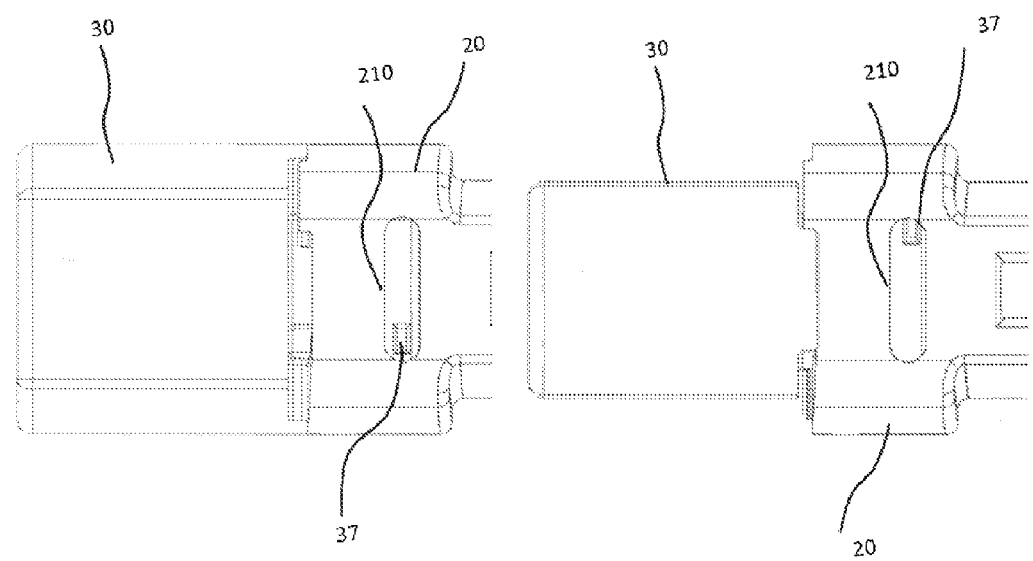
FIG. 10 shows an embodiment of the locking interface of the inner shaft and the outer shaft.

Referring to FIG. 10, in a particular embodiment, the outer shaft 20 comprises a window 210 indented from the outer surface to the inner surface of the outer shaft. A hump 37 on the knob of the inner shaft 30 slides from an edge of the window at the first position (left image) to an opposite edge of the window at the second position (right image), when the inner shaft rotates about 90 degrees. The outer shaft also includes windows 210 to facilitate molding of the hollow cavity to hold inner shaft therewithin. In some embodiments, the window 210 and the hump 37 that interacts with the window in order to lock or unlock the inner shaft to the outer shaft is replaceable by an interface and a complementary interface that are functionally equivalent to them. In some embodiments, the interface and the complementary interface comprise threaded fittings. In some embodiments, the interface and the complementary interface comprise a spring. In some embodiments, the interface and the complementary interface comprise a clamp. In some embodiments, the interface and the complementary interface comprise a latching element and a latchable element. In some embodiments, the interface and the complementary interface comprise a magnetic element. In some embodiments, the interface and the complementary interface comprise a deformable element. In some embodiments, the hump 37 is a usable operable element, for example, the hump 37 is supported by a spring force so that it can be pushed in to unlock from the window 210. In some embodiments, the hump 37 is a flexible element so that it deforms to lock or unlock to the outer shaft. In some embodiments, the inner shaft is injection moldable.

Humps:

In some embodiments, the knob includes at least one hump. In some cases, a second hump is configured to indicate the unlocking of the inner shaft from the outer shaft. In some cases, a second hump is guided into part of the groove when the inner shaft or the knob is at the first position. The first hump is at the edge of the window and the groove, slidable to pull the inner shaft out. The first and the second hump are aligned in a direction perpendicular to the rotation plane of the knob. The first and second hump are spatially offset by at least 5 mms and no greater than 5 cm.

In some embodiments, the width of the window is configured to allow the first hump to sit at one window edge at a first position and sit at a second window edge at a second position.

In some embodiments, the first position is the unlocked position of the inner shaft to the outer shaft. The first position is the locked position of the implant body to the inner shaft while the second position is the unlock position of the implant body to the inner shaft. The second position is the locked position of the inner shaft to the outer shaft.

In some embodiments, the inner shaft body includes at least one hump. In some embodiments, the outer shaft body includes at least an interface, i.e., a protrusion to interact with the hump. In some embodiments, the hump and the interface interacts to prevent the inner shaft from accidentally backing out after being inserted in the outer shaft.

Figure 11:
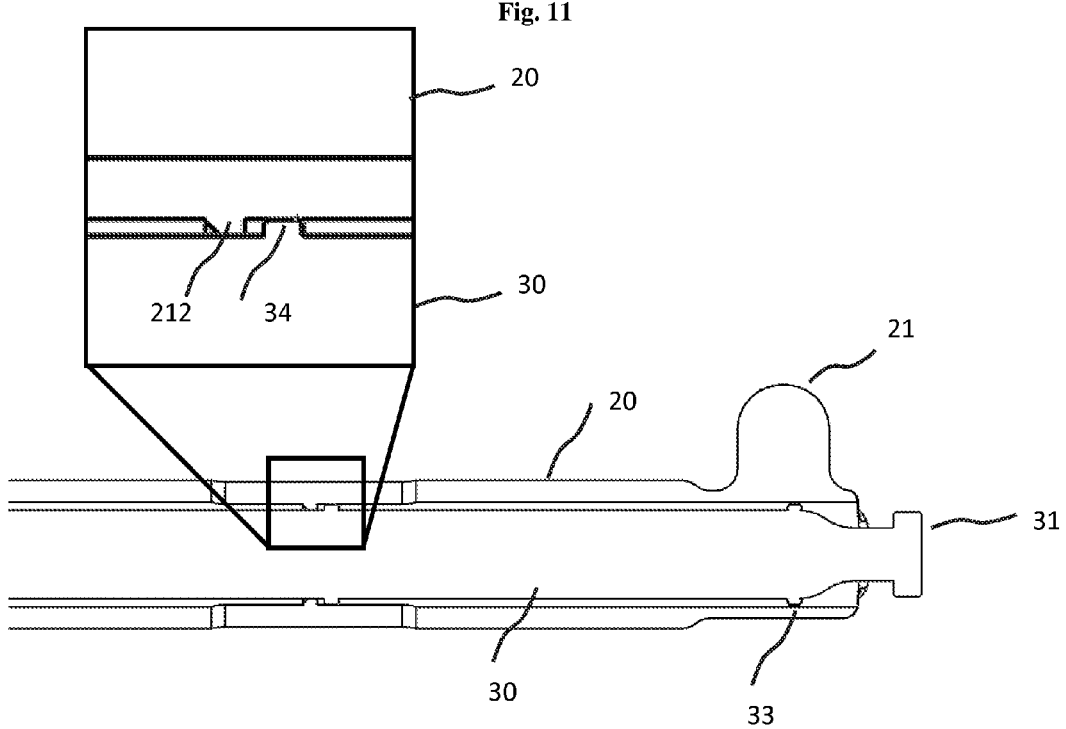
FIG. 11 shows an embodiment of preventing the inner shaft from being accidentally removed from the outer shaft.

Referring to FIG. 11, in a particular embodiment, an inner shaft 30 is properly inserted into an outer shaft 20. In some embodiments, the inner shaft includes at least two symmetrically located humps 33 to ensure concentric rotation of the inner shaft within the outer shaft. In some embodiments, the inner shaft tip 31 is not enclosed by the outer shaft 20. The insertion stopper 21 is located close to the insertion end of the outer shaft 20. The inner shaft body includes a hump 34 that interacts with an interface 212, i.e. a ramped protrusion to lock the inner shaft body 30 within the outer shaft 20.

Positions:

In some embodiments, the implant insertion devices are configurable in at least a first position and a second position. In some embodiments, the implant insertion devices are configurable in at least two different positions, i.e., an unlocked position and a locked position. In some embodiments, at the first position, the inner shaft is unlocked to the outer shaft. In some embodiments, when the implant body is properly loaded, the implant body is locked to the inner shaft at the first position. Further, the implant body is also attached to the outer shaft via an interface and a complementary interface. In some embodiments, the implant is properly locked, and the insertion device is ready for implant insertion. In some embodiments, at least one hump of the knob is at the edge of the corresponding window on the outer shaft, and the hump is ready to slide out a groove on the inner surface of the outer shaft so as to unlock the inner shaft from the outer shaft.

In some embodiments, at the second position, the inner shaft is locked to the outer shaft. In some embodiments, the implant body is unlocked to the inner shaft at the second position, thus releasable from the insertion device. In some embodiments, the implant body is still attached to the outer shaft via an interface and a complementary interface. In other embodiment, the implant body slightly detached from the outer shaft via an interface and a complementary interface. In some embodiments, the implant body is ready to be released from the implant insertion device at the second position. In some embodiments, at least one hump of the knob is at the opposite edge of the corresponding window on the outer shaft, and the hump locks the inner shaft to the outer shaft. In some embodiments, the second position is the loading position to load an implant body on the implant insertion device in order to properly lock the implant body to the inner shaft at the first position. In other embodiments, the implant body is loadable at the first position if switching to the second position enters the properly loading procedure afterwards. In some cases, the implant body is held tightly or locked to the insertion device when the inner shaft is configured at a first position such that the camp feature rests on the 'distal most' or 'higher' of the two different surfaces of the base. In some cases, the implant body is released or not held tight against the implant insertion device when the inner shaft is configured at a second position such that the cam rests at a "proximal most" or "lower" of the two different surfaces.

Outer Shaft Tips:

In some embodiments, the outer shaft includes two outer shaft tips proximal to the outer shaft opening at the insertion end of the outer shaft. In some embodiments, each of the two outer shaft tips holds one side slot of the two side slots of the implant body when the implant body is locked to the outer shaft. In some embodiments, In some embodiments, the outer shaft tips are symmetrically adjacent to the outer shaft opening. In some embodiments, two outer shaft tips are each of a semi-cylindrical shape. In some embodiments, a cross section of each of the two outer shaft tips is a semi-ellipse. In some embodiments, a cross section of each of the two outer shaft tips is a rectangle. In some embodiments, a cross section of each of the two outer shaft tips is a semi-rectangle. In some embodiments, a cross section of each of the two outer shaft tips is a triangle. In some embodiments, a cross section of each of the two outer shaft tips is a circle sector. In some embodiments, a cross section of each of the two outer shaft tips is a circle. In some embodiments, a cross section of each of the two outer shaft tips is a trapezoid. In some embodiments, a cross section of each of the two outer shaft tips is a pentagon or a rhombus. In some embodiments, the cross section of each of the two outer shaft tips is a parallelogram. In some embodiments, a cross section of each of the outer shaft tips is an arbitrary two dimensional shape.

In some embodiments, the outer shaft tips are on the outer surface of the outer shaft. In some embodiments, the outer shaft tips are attached on the outer surface of the outer shaft. In some embodiments, the outer shaft tips are protrusions extending from the outer surface of the countershaft. In some embodiments, the outer shaft tips are protrusions extending from the outer surface of the countershaft toward the implant insertion direction. In some embodiments, the outer shaft tips extend along the longest axis of the outer shaft from the insertion end of the outer shaft.

Outer Shaft Openings:

In some embodiments, the outer shaft includes an opening that allows passage of the inner shaft tip from the insertion the outer shaft to the exertion of the outer shaft. In some embodiments, the outer shaft opening has a cross section that is substantially identical to the cross section of the inner shaft tip. In some embodiments, the outer shaft opening has a longest axis that is substantially identical to the longest axis of the cross section of the inner shaft tip. In some embodiments, the axis is a straight line connecting two points on the closing contour of a two dimensional shape. In some embodiments, the longest axis is the longest straight line connecting two points on the closing contour of a two dimensional shape.

In some embodiments, the outer shaft opening is cylindrical. In some embodiments, the cross section of the outer shaft opening is an ellipse. In some embodiments, the cross section of the outer shaft opening is a rectangular. In some embodiments, the cross section of the outer shaft opening is a rhombus. In some embodiments, a cross section of the outer shaft opening is a triangle. In some embodiments, the cross section of the outer shaft opening is a parallelogram. In some embodiments, preferred by a molding process, the outer shaft opening is circular.

Outer Shaft Bodies:

In some embodiments, the outer shaft body is hollow so as to accommodate an inner shaft body therewithin. In some embodiments, the outer shaft body has a straight rod-shape. In other embodiments, the outer shaft body is curved.

In some embodiments, the outer shaft body includes a plurality of windows. In some embodiments, the windows are indented into the outer shaft body from the outer surface and connect with a hollow cavity therewithin. In some embodiments, the windows are configured to facilitate injection molding of the hollow cavity within the outer shaft. In some embodiments, the windows from two opposite sides of the outer surface are formed by mold parts comprising interleaved protrusions such that the internal cavity of the outer shaft is formed by the continuous points of contact among the interleaved protrusions. In some cases, the windows are artefactual remnants of the use of the intercalated protrusions in the molding process. In some embodiments, the windows are interleaved such that the overlapping areas are relatively small comparing to the length of the outer shaft body. Such small areas of overlap facilitate the support and endurance of force and pressure of the outer shaft during an insertion. In certain embodiment, the overlapping area of two adjacent windows from two opposite sides of the outer shaft forms a through hole between the two opposite sides of the outer shaft. Therefore, the through hole reduces support and endurance of force and pressure the outer shaft. In some embodiments, a curved outer shaft accommodates a flexible inner shaft therewithin. In some embodiments, a curved outer shaft is configured to facilitate implant insertion at a narrow angle determined by the patient's anatomy or medical conditions.

In some cases, use of intercalating protrusions to create an internal cavity in the outer shaft allows casing of a bent or curved outer shaft, which is difficult to achieve with an injection mold part that would need to be removed after casting.

In some embodiments, the outer shaft body has an outer face. In some embodiments, the window is not extended to the outer face of the outer shaft. In some embodiments, the outer face has a close contour. In some embodiments, each window has its width along the base-to-tip direction of the outer shaft. In some embodiments, each window has its width greater than its length, the length being in a direction perpendicular to the base-to-tip direction. In some embodiments, the base-to-tip direction is a curved line. In other embodiments, the base-to-tip direction is a spline fitted to the curved central line of the outer shaft body from the base to the tip.

Figure 12:
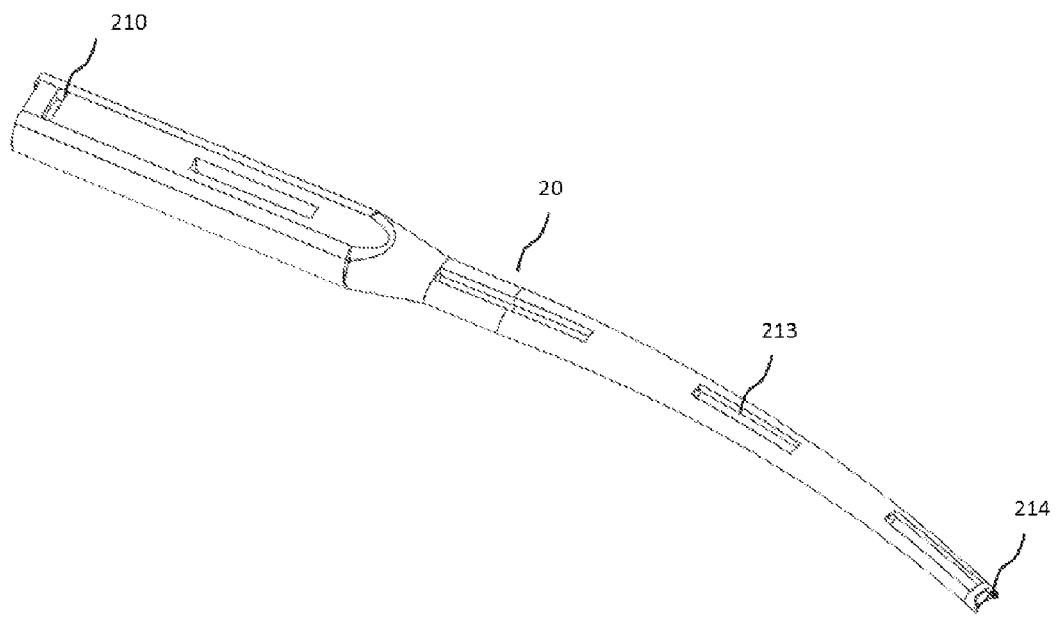
FIG. 12 shows an embodiment of the implant insertion device.

Referring to FIG. 12, in some embodiments, the outer shaft body is curved. The outer shaft 1220 includes a window 210 that locks or unlocks to the hump of the knob. The outer shaft has a curved outer face 214. The outer shaft has interleaved windows 213 from opposite sides of the outer surface overlapping so as to generate a continuous hollow cavity to fit inner shaft therewithin.

Figure 13:
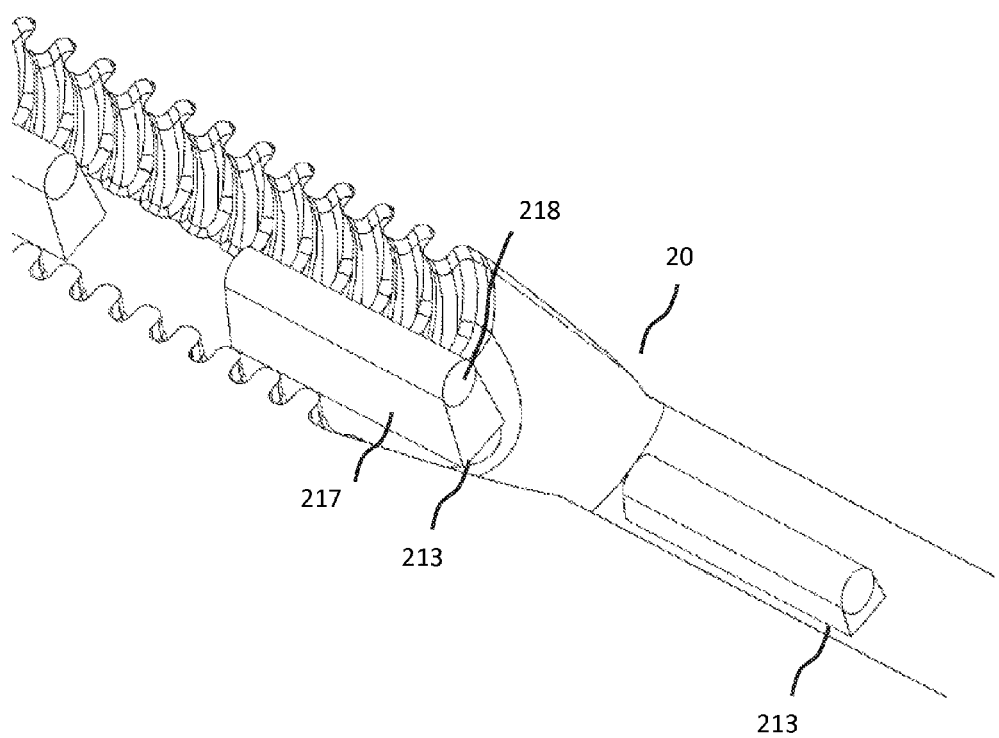
FIG. 13 shows molds to make the implant insertion device of FIG. 12.

Referring to FIG. 13, in a particular embodiment, molds for creating the inner surface of the outer shaft body is shown. In some embodiments, the outer shaft body 20 has an inner surface generated by interleaved molds from two opposite sides of the outer surface. An intercalated mold includes a protruding volume that is substantially cylindrical 218 to create an internal space to hold a substantially cylindrical inner shaft body therewithin. The interleaved mold also includes an additional volume 217 that connects with the cylindrical volume 218 to create a window 213 which is indented from the outer surface of the outer shaft 20. The intercalating nature of the mold features that produce the indented windows 213 intercalate to generate a continuous internal space to allow an inner shaft body to fit therewithin.

Locking and Unlock Mechanisms:

In some embodiments, the implant body is properly locked to the outer shaft, when each of the two side slots fits to one of the two outer shaft tips. In some embodiments, the fitting of each of the two side slots to one of the two outer shaft tips, when the implant body the implant body is properly locked to the outer shaft, is configured to hold the implant body fixed to the implant insertion device. In some embodiments, the implant body is properly locked to the implant insertion device when each of the two side slots of the outer shaft fits to one of the two outer shaft tips, and the inner shaft is locked to the implant body. In some embodiments, the implant body is first locked to the inner shaft and then locked to the outer shaft. In other embodiments, the implant body is first locked to the outer shaft with an inner shaft properly inserted therewithin then locked to the inner shaft. In some embodiments, the implant body is locked to the inner shaft and the outer shaft substantially simultaneously when the inner shaft is properly inserted within the outer shaft. In some embodiments, the implant is properly locked to the insertion device by a rotation of the knob. In some embodiments, the rotation of the knob should be timely controlled so that there is some engagement between inner shaft tip and the implant body. In some embodiments, the timely controlled rotation is configured to position the ramp with respect to the matching notch so that the motion does not pull inner shaft away from the implant before the inner shaft tip can pull implant toward the outer shaft.

In some embodiments, the proper locking of the implant body to the outer shaft is configured to facilitate reduction of pressure on the implant body during insertion. In some embodiments, the proper locking of the implant body to the outer shaft is configured to eliminate rotation of the implant body with respect to the implant insertion device during insertion. In some embodiments, the proper locking of the implant body to the outer shaft is configured to eliminate rotation of the implant body. In some embodiments, the proper locking of the implant body to the outer shaft is configured to reduce unwanted implant release from the implant insertion device during insertion. In some embodiments, the proper locking of the implant body to the outer shaft increases the area of interaction between the implant body and the implant insertion device. In some embodiments, the proper locking of the implant body to the outer shaft increases the area of interaction with the implant body so that the force on the implant body is partly transferred to the implant insertion device. In some embodiments, the proper locking of the implant body to the outer shaft is configured to reduce the pressure on the implant body. In some embodiments, the proper locking of the implant body to the outer shaft is configured to decrease the risk of implant breakage. In some embodiments, the proper locking of the implant body to the outer shaft is configured to decrease the risk of unwanted implant detachment from the implant insertion device.

In some embodiments, the implant body is properly unlocked from the outer shaft when each of the two side slots disassociate from one of the two outer shaft tips. In some embodiments, the implant body is properly unlocked from the implant insertion device when the implant body is properly unlocked from the inner shaft tip. In some embodiments, the implant body is properly unlocked to the implant insertion device when each of the two side slots of the outer shaft disassociates from previously fitted outer shaft tip, and the inner shaft is unlocked to the implant body. In some embodiments, the implant body is first unlocked from the inner shaft and then unlocked from the outer shaft. In other embodiments, the implant body is first unlocked from the outer shaft with an inner shaft properly inserted therewithin then unlocked to the inner shaft. In some embodiments, the implant body is unlocked from the inner shaft and the outer shaft substantially simultaneously when the inner shaft is properly inserted within the outer shaft. In some embodiments, the implant is properly unlocked to the insertion device by a rotation of the knob. In some embodiments, the rotation of the knob should be timely controlled so that there is some disassociation between inner shaft tip and the implant body. In some embodiments, the timely controlled rotation is configured to position the ramp with respect to the matching notch so that the motion pull outer shaft away from the implant before the inner shaft tip can unlock the implant body.

In some embodiments, the implant body is only properly lockable to the implant insertion device when it is first loaded onto the inner shaft when the inner shaft is locked to the outer shaft. In some embodiments, the outer face of the outer shaft is shaped so as to enable proper locking of the implant body only when the inner shaft is locked to the outer shaft. In some embodiments, the implant body is properly lockable to the implant insertion device when it is first loaded onto the inner shaft when the inner shaft is locked or unlocked to the outer shaft.

Kits:

In certain embodiments, kits comprising at least one insertion device and or at least one implant body as disclosed herein, sealed in a sterile container, are disclosed herein. In some embodiments, a first kit cover is a sealed cover enclosing at least one implant insertion device and at least one implant body. In some embodiments, a first kit cover is a sealed cover enclosing at least one implant insertion device and at least two implant bodies. In some embodiments, the enclosed implant bodies are configured to be properly locked or unlocked to the enclosed implant insertion device within the kit. In some embodiments, the contents held in the first kit cover are sterile. In some embodiments, a first kit cover is peelably sealed. In some embodiments, the first kit cover is hermetic but peelably sealed. In some embodiments, a second kit cover is a sealed cover enclosed in the first kit cover. In some embodiments, the contents held within the second kit cover are sterile. In some embodiments, the second cover is peelably sealed. In some embodiments, the second kit cover is hermetic but peelably sealed. In some embodiments, properly opening the first kit cover does not affect the sealing of the second kit cover.

In some embodiments, the kit includes a device tray, a device holder, or use of the same. In some embodiments, the device tray or holder has at least one compartment. In some embodiments, the at least one compartment is configured to securely hold an implant insertion device, an implant, or both. In some embodiments, the device tray is configured to securely protect the implant insertion device and/or implant from damages. In some embodiments, the kit has compartments to hold the implant insertion device and/or implant individually or together in a locked configuration. In some embodiments, the kit encloses at least one implant body therewithin. In some embodiments, the kit encloses at least one implant insertion device therewithin.

In some embodiments, the device tray and the kit cover is for single-use only. In some embodiments, the device tray and the kit cover are not for reuses after the inner most kit cover has been opened. In some embodiments, the inner most kit cover is the first or the second kit cover.

Disclosed herein are sterile kits enclosing the implant insertion devices and/or implant bodies as disclosed herein, for example, a kit with two different kit covers, at least the inner-most kit cover encloses contents that are sterile. These contents include at least an implant insertion device, each implant insertion device having an outer shaft and an inner shaft that can be inserted and locked to the outer shaft, and/or at least an implant body, having at least two interfaces to lock to the inner shaft and/or the outer shaft independently. Some kit comprises an individual kit cover for each individual implant body, for example, as the inner-most kit cover, each implant body having at least two interfaces to lock to the inner shaft and/or the outer shaft independently, the kits enclosing individual sterile implant bodies are then packed in an outer layer of kit cover.

Anatomical Planes:

In some embodiments, the longitudinal plane is formed by the left-to-right axis and the anterior-to-posterior axis of a subject. In some embodiments, the longitudinal axis of is the head to toe axis of a subject. In some embodiments, the coronal plane is a plane formed by the left to right and the head-to-toe axis of a subject. In some embodiments, the sagittal plane is the plane formed by the anterior to posterior axis and the head-to-toe axis of a subject.

In some embodiments, the left-to-right axis is an anatomical axis defined by a subject's left to the subject's right. In some embodiments, the head-to-toe axis is an anatomical axis defined by a subject's head to the subject's feet. In some embodiments, the anterior-to-posterior axis is an anatomical axis defined by a subject's belly to the subject's back.

In some embodiments, a height of an object is the along the head-to-toe axis, when the object is properly deployed in a subject. In some embodiments, a width of an object is the along the left-to right-axis, when the object is properly deployed in a subject. In some embodiments, a length of an object is the along the anterior-to-posterior axis, when the object is properly deployed in a subject.

In some embodiments, the implant body has a non-uniform height to accommodate the lordosis or kyphosis angle of the spinal cord. In some cases, the longitudinal plane is a plane formed substantially by the left-to-right axis and the anterior-to-posterior axis of a subject.

Implant Insertion Directions:

In some embodiments, the implant is inserted from the anterior to the posterior direction of the patient. In other embodiments, the implant is inserted from the posterior to the anterior direction of the patient. In some embodiments, the implant is inserted from the left to the right direction of the patient. In some embodiments, the implant is inserted from the right to the left direction of the patient. In some embodiments, the implant is inserted from a direction determined by the operational angle of the patient and then rotated into its proper location.

Cam Features:

In some embodiments, the insertion device includes a cam feature that translates a rotation of the inner shaft into a linear movement of the inner shaft with respect to the outer shaft. In some cases, a cam feature is attached to the top-most cross-section of the knob. In some cases, the cam feature faces the bottom-most cross section of the outer shaft. In some cases, the cam feature faces the base of the outer shaft. In some cases the outer shaft includes at least one cam feature that is attached to the bottom-most cross section of the outer shaft. In some cases, the knob includes at least one cam feature that is attached to the top-most cross section of the knob that does not go into the outer shaft. In some cases, the cam feature faces the top-most cross-section of the outer shaft. In some cases, the cam feature faces the top of the knob.

In some embodiments, the cam feature includes at least a step feature. In some cases, the cam feature includes at least a step, wherein the step starts at the top-most cross section of the knob and rises toward the insertion end of the inner shaft. In some cases, the cam feature includes an upward ramp feature and a downward ramp feature, wherein the upward and downward ramp is substantially vertical to the top-most cross section of the knob. In some cases, the cam feature includes an upward ramp feature and a downward ramp feature, wherein each plane of the upward ramp and downward ramp have an acute angle with the top-most cross section of the knob. In some cases, the upward ramp extends from a cross sectional that is closer to the bottom-most cross section toward the insertion end of the inner shaft. In some cases, the downward ramp extends from a cross sectional that is closer to the top-most cross section toward the bottom-most cross section of the inner shaft. In some cases, the cam feature has a step feature with a uniform height extending from the top-most cross section of the knob toward the insertion end of the inner shaft. In some cases, the cam feature is a dent feature with a uniform depth extending from the top-most cross section of the knob toward the bottom most-cross section of the knob. In some cases, the cam feature is a three dimensional shape including a plane with an upward ramp. In some cases, the cam feature is a three dimensional shape including a plane with a downward ramp. In some cases, the cam feature is a three dimensional shape including a plane with an upward and a downward ramp. In some cases, the cam feature is cylindrical. In some cases, the cam feature is cylindrical with a cross section of a circle sector. In some cases, the cam feature is cylindrical with a cross section of a portion of a circle sector. In some cases, the cam feature is cylindrical with a cross section of a triangle. In some cases, the cam feature is cylindrical with a cross section of a rhombus. In some cases, the cam feature is cylindrical with a cross section of a trapezoid. In some cases, the cam feature is cylindrical with a cross section of a pentagon. In some cases, the cam feature is cylindrical with a cross section of a parallelogram. In some cases, the cam feature is an arbitrary three dimensional shape that attaches to the bottom-most cross section of the outer shaft. In other cases, the cam feature is an arbitrary three dimensional shape that attaches to the top-most cross section of the knob.

In some embodiments, the outer shaft includes at least two different surfaces at the bottom of the outer shaft facing the cam feature. In some cases, the knob includes at least two different surfaces at the top-most cross section of the knob that does not go into the outer shaft facing the cam feature. In some cases, the two different surfaces allow a cam feature to slide on. In some cases, one of the two different surfaces includes a first position or an unlocked position of the inner shaft to the outer shaft. In some cases, the other of the two different surfaces includes a second position or a locked position of the inner shaft to the outer shaft. In some cases, one of the two different surfaces which includes a first position or an unlocked position of the inner shaft to the outer shaft is closer to the base of the insertion device. In some cases, the other of the two different surfaces which includes a second position or a locked position of the inner shaft to the outer shaft is closer to the tip of the insertion device. The offset of the two different surfaces determines the linear displacement that an inner shaft tip moves with respect to the outer shaft.

In some embodiments, the two different surfaces are connected by a ramp feature. In some cases, one of the two different surfaces connects to the edge of the ramp that is closer to the base of the knob. In yet certain cases, the other of the two different surfaces connects to the edge of the ramp that is closer to the insertion end of the device.

In some embodiments, the height of the ramp determines the linear displacement of the inner shaft tip with respect to the outer shaft. In other cases, the length and the acute tilted angle of the ramp from the two different surfaces determines the linear displacement of the inner shaft tip with respect to the outer shaft. In some cases, the displacement of the inner shaft is along the direction from the base toward the tip of the insertion device.

Referring to FIG. 9, in some embodiments the base of the outer shaft includes at least two different surfaces at the bottom of the outer shaft facing the top of the knob. In some cases, the outer shaft 20 includes a first surface 22, or 26 and a second surface 24 or 28 that a cam feature of the knob slides on. A ramp element, 23 or 27, connects the first and second surfaces. The outer shaft also has a stopper 25 or 29 that stops the sliding of the cam feature from the first position to the second position, or from the second position to the first position. The outer shaft also includes a groove 211 at the inner surface of the outer shaft that a hump of the knob can slide along. The outer shaft also has a window 210 indented from the outer surface to the inner surface of the outer shaft. The edge of the window connects with the groove so that the hump can slide along the groove 211 into the window 210. At the first position, the hump is aligned with the groove 211 and the window 210 edge connecting to the groove 211. The camp is on top of surfaces 22 and 26. When the inner shaft rotates about 90 degrees to the second position, the hump is at the opposite edge of the window 210. The hump feature and the window 210 prevent the inner shaft from being removed from the outer shaft while inner shaft is in unlocked with respect to an implant body. The inner shaft cam is on top of surfaces 28 and 24 at the second position.

Figure 14:
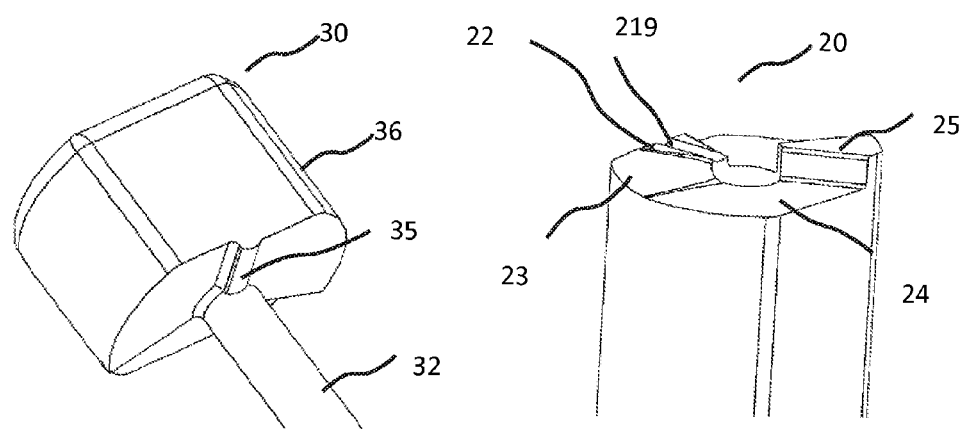
FIG. 14 shows an embodiment of the knob of the inner shaft and the base of the outer shaft.

Referring to FIG. 14, in a particular embodiment, the base of the outer shaft includes at least two different surfaces at the bottom of the outer shaft facing the top of the knob. In some embodiments, the outer shaft 20 (right image) includes a first surface 22 and a second surface 24 that a cam feature of the knob slides thereon. A ramp element, 23 connects the first surface, 22 and the second surface, 24. The outer shaft also has a stopper 25 that stops the sliding of the cam feature from the first position to the second position, or from the second position to the first position. In some cases, the knob of the inner shaft 30 includes a cam feature 35 that slides on the first and the second surfaces and the ramp features of the outer shaft to transform rotation of the inner shaft into linear displacement of the inner shaft tip. The inner shaft body 32 is connected to the top of the knob 36. The groove 219 is configured to providing tactile feedback in the locking or unlocking of the inner shaft to the outer shaft. The groove 219 is optional in some embodiments.

Figure 15:
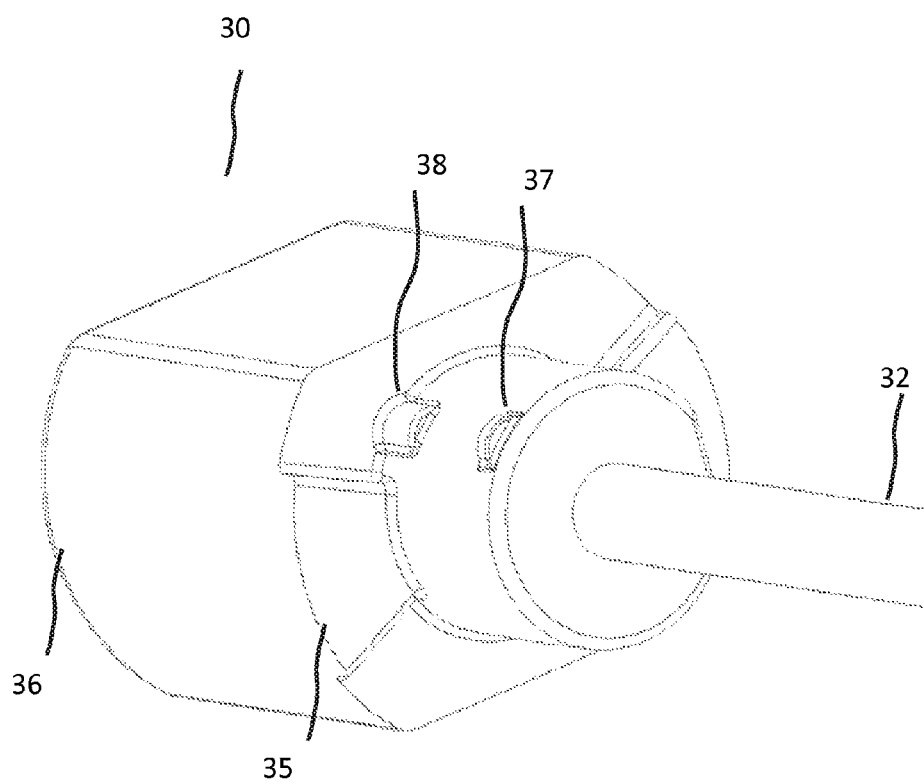
FIG. 15 shows an embodiment of the knob of the inner shaft.

FIG. 15 shows the inner shaft body 30 in an exemplary embodiment. The inner shaft body comprises a knob 36 at the base of the inner shaft 30, and the inner shaft body 32 connects to the top of the knob 36. The knob 36 comprises a hump 37 for interacting with the complementary window on the outer shaft so at to lock or unlock the inner shaft to the outer shaft. The knob also comprises at least one cam 35 that slides on the base of the outer shaft while the inner shaft rotates within the cavity of the outer shaft. Optionally, the knob comprises a hump 38 for providing tactile feedback in the locking or unlocking of the inner shaft to the outer shaft. The hump 38 interacts with a groove on the inner surface of the outer shaft so as to provide slight resistance and a snap tactile feel to the user during locking or unlocking of the inner shaft to the outer shaft. In some cases, the hump 37 supported by a spring force so that it can be pushed in to unlock from the window on an outer shaft. In some cases, the hump 37 is a flexible element so that it deforms to lock or unlock to the outer shaft. In some cases, the inner shaft is injection moldable.

Figure 16:
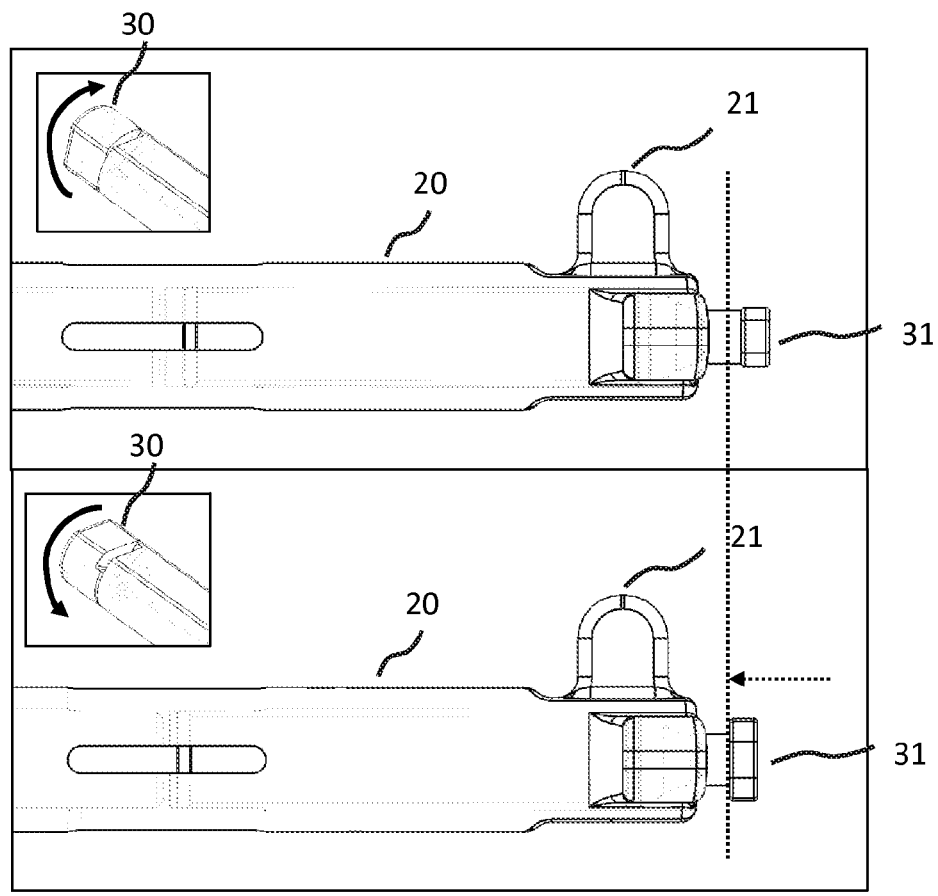
FIG. 16 shows an embodiment of the rotation of the inner shaft and linear movement of the inner shaft with respect to the outer shaft so as to lock the implant body to the implant insertion device.

FIG. 16 shows an exemplary embodiment of a cam feature in locking an implant body to the inner shaft. A cam feature located on the knob of the inner shaft 30 on the top surface of the knob facing the base of the outer shaft 20. Rotation of the knob 30 allows a cam feature to slide on a ramp feature of the outer shaft so as to transform the rotation into a linear movement of the inner shaft tip 31. At a second position (top image), the inner shaft tip 31 extends further away from the outer shaft 20, the implant is not locked to the inner shaft tip 31. At a first position (bottom image) the inner shaft tip 31 is rotated 90 degrees and also pulled closer to the outer shaft 20 and to the insertion stopper 21, thus the implant body is locked between the outer shaft 20 and the inner shaft tip 31.

Detectable Tags:

In some embodiments, detectable tags are compounds or compositions that are detectable to one or more medical imaging or detection modalities. Non-limiting examples of medical imaging or detection modalities are one or more selected from: MRI, MRI-PET, CT, x-ray, ultrasound, OCT, fluorescence, bioluminescence, PET, SPECT, microPET, and microSPECT. In some cases radio-opaque material such as barium sulfate is added to resin before the injection molding process as to provide radio-opacity to the instruments. A range of 1% to 40% of barium sulfate, or equivalent, concentration (weight/weight) may be used.

Methods:

Also disclosed herein are methods related to use of individual components or entities of the implant insertion devices and/or the implant bodies disclosed herein, for example, for the delivery of a graft tissue to the intervertebral space of a patient. Some methods related securing an implant body to an implant insertion device, for example, by rotating an inner shaft such that at least one cam at the base of the inner shaft moves from a first position to a second position displaced by a distance sufficient to pull an implant body thereby locking it in place against an outer surface of an insertion device. Simultaneously, by rotating the inner shaft, the inner shaft tip rotates in the chamber of the implant body so that it locks the implant body to the inner shaft at the second position. Some method related to reversely unlock an implant body from an insertion device after the implant body is properly delivered, for example by reversely rotating an inner shaft such that the implant body is unlocked from the inner shaft and is readily removable from the insertion device.

"About":

In some embodiments, "about" is used to indicate a −10% to a 10% range about a central number. For example, "about 100" means a range of at least 90 to no more than 110.

EXAMPLES

The following illustrative examples are representative of embodiments of the devices and methods described herein and are not meant to be limiting in any way.

Example 1

A sterilely-packed single-use only implant delivery system as disclosed herein is used to deliver an implant and a graft tissue to an intervertebral space of a patient. The implant delivery system includes an implant insertion device and an implant body. These implant insertion devices are injection molded. The device is discarded after a single use. This medical procedure is repeated in multiple hospitals on 100 patients in need of a spinal implant using the injection moldable single-use devices. Each procedure is performed with a new, single sterilely packed injection moldable device which is discarded after a one-time usage. A machine crafted, reusable implant delivery device is used to insert an implant to the intervertebral space of a patient. The reusable device is cleaned and sterilized on-site and/or off-site between usages. The medical procedure is repeated in hospitals on 100 patients using the reusable devices. The post-procedure infection is monitored in all 200 patients. A substantially higher device-related infection is found in patients operated by reusable devices than those by single-use devices.

Example 2

A sterilely-packed single-use only implant delivery system as disclosed herein is used to deliver an implant and a tissue to an intervertebral space of a patient. The implant delivery system includes an implant insertion device and an implant body. These implant insertion device is injection molded and discarded after a single use. This medical procedure is repeated in multiple hospitals on 80 patients in need of a spinal implant using the injection moldable single-use devices. Each procedure is performed with a new, single sterilely packed injection moldable device which is discarded after a one-time usage. In comparison, a machine crafted, reusable implant delivery device is used to insert an implant to the intervertebral space of a patient. The reusable device is cleaned and sterilized between usages. The medical procedure is repeated in hospitals on 80 patients using the reusable devices. The post-procedure infection is monitored in all 160 patients. A significantly higher cost per usage is found with the reusable device when compared to the single-use injection moldable device. The cost of reusable device includes the cost of cleaning, sterilization, transportation to offsite professional cleaning facilities, packing after cleaning, transportation after cleaning back to hospitals, and additional treatment costs to device-related infections.

Example 3

A sterilely-packed single-use only implant delivery system as disclosed herein is used to deliver an implant and a tissue to an intervertebral lumbar space of a patient. The implant delivery system includes an implant insertion device and an implant body. These implant insertion devices are injection molded. The device is discarded after a single use. This medical procedure is repeated in multiple hospitals on 80 patients in need of a spinal implant using the injection moldable single-use devices. Each procedure is performed with a new, single sterilely packed injection moldable device which is discarded after a one-time usage. A machine crafted, reusable implant delivery device is used to insert an implant to the intervertebral space of a patient. The reusable device is cleaned sterilized on-site and/or off-site between usages. The medical procedure is repeated in hospitals on 80 patients using the reusable devices. The post-procedure infection is monitored in all 160 patients. A significantly higher cost per usage is found with the reusable device when compared to the single-use injection moldable device. In particular, 80 implant delivery devices of the present invention are injection molded along with implant bodies with 10 different dimensions that fits in various locations of the spinal cord. 80 traditional reusable implant insertion devices with implant bodies of different dimensions are machined. The cost of injection molding and machining of a same number of implant delivery devices and implant bodies are compared. The cost of materials is also compared for two different manufacturing processes. The cost of injection molding is significantly lower than machine-crafting an implant delivery device or an implant with the identical dimensions. The packing and sterilization cost for each implant delivery device is also greatly lower than that of each traditional reusable implant insertion.

Example 4

A sterilely-packed single-use only implant delivery system as disclosed herein is used to deliver an implant and tissue to an intervertebral space of a patient. The implant delivery system includes an implant insertion device and an implant body. These implant insertion devices are injection molded. The device is discarded after a single use. Radio frequency (RF) tags are loaded on the implant to guide the procedure with real-time imaging. The implant body is securely locked to the inner shaft body by a rotation of the inner shaft in the chamber of the implant body. Further, the implant body is also locked to the outer shaft by fitting an interface of the implant body securely to the complementary interface at the insertion end of the outer shaft. The implant is securely fastened to the implant delivery device so that it protects the implant from undesired rotation or breakage during the procedure of implant insertion. The procedure is repeated for 10 times. A different implant delivery device not disclosed herein with no proper secure locking of the implant body to inner shaft or the outer shaft of the implant delivery device is also used for spinal insertion in a patient. The procedure is performed for 10 patients with not securely locked insertion device. The insertions of implants are successful as indicated by the radio frequency tags of the implant in all 10 patients with securely locked implant. For the other 10 patients, the implant body wobbles and rotates on the delivery device in some of those procedures, as indicated by the RF tags, when the implant body experiences uneven friction from the tissue. In addition, the undesirable breakage of implant bodies at the unlocked interface is significantly higher than that of the securely locked implant bodies possibly due to extreme pushing forces exerted only on the small connecting surface of the unlocked interface.

Example 5

A sterilely-packed single-use only implant delivery system as disclosed herein is used to deliver an implant and a tissue to an intervertebral space of a patient. The implant delivery system includes an implant insertion device and an implant body. These implant insertion devices are injection molded. The device is discarded after a single use. This medical procedure is repeated in multiple hospitals on 100 patients in need of a spinal implant using the injection moldable single-use devices. Each procedure is performed with a new, single sterilely packed injection moldable device which is discarded after a one-time usage. A machine crafted, reusable implant delivery device is used to insert an implant to the intervertebral space of a patient. The reusable device is cleaned sterilized on-site and/or off-site between usages. The medical procedure is repeated in hospitals on 100 patients using the reusable devices. The implant delivery devices and implant bodies are packed in a kit with two pealably sealed kit covers. The first kit cover is not sterile. Within the first kit cover, individual sterile covers are contained to securely an implant delivery device and an implant body in each sterile kit cover. Each second kit contains implant insertion device implant body of different sizes for procedures of different surgical needs. Optionally, the implant is securely locked to the implant delivery device so that it reduces the device handling in a procedure. Upon arrival in the operation suite, the first kit cover is removed before or upon arrival at the operation suites. Right before operation, a sterile kit with the right implant shape and size is selected to be opened to keep the device and implant body therewithin sterile. A biocompatible material is injected before or after the implant insertion into the internal space of the implant for spinal fusion. After implant insertion, the implant delivery device is disposed.

Example 6

A sterilely-packed single-use only implant delivery system as disclosed herein is used to deliver an implant and a tissue to an intervertebral space of a patient. The implant delivery system includes an implant insertion device and an implant body. These implant insertion devices are injection molded. The device is discarded after a single use. Each implant delivery system is injection molded in separated pieces, these pieces includes an inner shaft, an outer shaft, and an implant body. The implant bodies and the implant delivery devices are molded in different dimensions and sizes so that the implant body fits in the various intervertebral spaces between any two adjacent vertebral of the spinal cord.

Example 7

A sterilely-packed single-use implant delivery system as disclosed herein is used to deliver an implant and tissue to an intervertebral space of a patient. The implant delivery system includes an implant insertion device and an implant body. These implant insertion devices are injection molded. The device is discarded after a single use. Each implant delivery system is injection molded in separated pieces including an inner shaft, an outer shaft, and an implant body. The inner shaft is molded in two separated pieces including a knob and an inner shaft body together with the inner shaft tip. The inner shaft body and inner shaft tip are molded together using durable, medical imaging compatible metals to increase the durability of the inner shaft body and tip.

Example 8

A sterilely-packed single-use only implant delivery system as disclosed herein is used to deliver an implant and a tissue to an intervertebral space of a patient. The implant delivery system includes an implant insertion device and an implant body. These implant insertion devices are injection molded. The device is discarded after a single use. Radio frequency (RF) tags are loaded on the implant to guide the procedure with real-time imaging. The implant delivery system is used in a Magnetic Resonance Imaging (MRI) guided implant insertion procedure. Traditional machinable implant insertion devices made of magnetic metal are not compatible with MRI and causes detrimental accidents. Traditional machine-crafted implant device made of magnetic metal cannot be used in any MRI guided implant insertion. An injection moldable implant delivery device of the present invention made of non-magnetic MRI-compatible materials is safe to use for MRI guided implant insertion procedure. Radio frequency tags are attached to edges of the implant body before the procedure so that the real-time position of the implant body is MRI visible to ensure proper and accurate implant insertion.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. An implant delivery system comprising: an implant insertion device having a longitudinal axis, the device comprising:
   i) an inner shaft comprising: an inner shaft body extending along the longitudinal axis; a knob at a base of the inner shaft body, the knob comprising a first interface; an inner shaft tip at an insertion end of the inner shaft body, wherein the inner shaft tip is not substantially cylindrically circular; and
   ii) an outer shaft extending along the longitudinal axis and configured to hold the inner shaft body therein, the outer shaft having a proximal end having a proximal rim at the most proximal portion of the proximal end, the outer shaft comprising: a hollow outer shaft body, wherein the outer shaft body is configured to accommodate the inner shaft body therewithin; an outer face; an outer shaft opening at the outer face of the outer shaft; a first and a second window positioned on opposite sides of the outer shaft, wherein the first window and the second window are continuous with the hollow interior of the hollow outer shaft body, and wherein the first window and the second window overlap in part and do not overlap in part; and
   iii) a ramp that extends from the proximal rim of the outer shaft in a proximal direction that is parallel to the longitudinal axis; and
   wherein the inner shaft tip is configured to fit through a main slot of an implant body and rotate in a chamber of the implant body so as to lock the implant body to the inner shaft when the ramp interfaces with the first interface of the knob.

2. The device of claim 1, wherein the implant delivery system further comprises an implant body comprising a support structure comprising: an outer surface; a main slot indented into the outer surface; a chamber indented from the main slot, the chamber being deeper than the main slot; wherein the implant body is substantially toroidal.

3. The device of claim 1, wherein the implant insertion device is injection molded.

4. The device of claim 1, wherein the implant delivery system is for one-time use only.

5. The device of claim 2, wherein the internal space of the implant body is filled at least partly by at least one graft material.

6. The device of claim 1, wherein the inner shaft comprises at least one material selected from carbon fiber-reinforced polymer, carbon fiber-reinforced plastic, carbon fiber-reinforced thermoplastic, glass fiber-reinforced polymer, glass fiber-reinforced plastic, and polyarylamide.

7. The device of claim 1, wherein the inner shaft body is flexible so as to fit in a curved outer shaft body.

8. The device of claim 1, wherein the inner shaft tip is substantially rectangular cuboid or cylindrically elliptical.

9. The device of claim 1, wherein the ramp and first interface are portions of a cam feature comprising a stop that limits rotation of the inner shaft relative to the outer shaft to less than 180 degrees.

10. The device of claim 1, wherein the inner shaft tip is configured to fit and rotate in the chamber of the implant body.

11. The device of claim 1, wherein the inner shaft tip is configured to pass through the outer shaft opening.

12. The device of claim 1, wherein the ramp has a height that is substantially equal to a distance of a linear displacement of the inner shaft relative to the outer shaft when the inner shaft is rotated relative to the outer shaft.

13. The device of claim 1, wherein the outer shaft body is curved.

14. The device of claim 1, wherein the outer shaft comprises at least one material selected from the list consisting of carbon fiber-reinforced polymer, carbon fiber-reinforced plastic, carbon fiber-reinforced thermoplastic, glass fiber-reinforced polymer, glass fiber-reinforced plastic, and polyarylamide.

15. The device of claim 1, wherein the outer shaft is injection moldable.

16. The device of claim 1, wherein the outer shaft opening is configured to allow passage of the inner shaft tip.

17. The device of claim 1, wherein a movement of the inner shaft body relative to the outer shaft is determined by a height of the first interface or the second interface.

18. An implant delivery system comprising: an implant insertion device comprising:
   i) an inner shaft comprising: an inner shaft body; a knob at a base of the inner shaft body, the knob comprising a first interface; an inner shaft tip at an insertion end of the inner shaft body, wherein the inner shaft tip is not substantially cylindrically circular; and
   ii) an outer shaft configured to hold the inner shaft body therein, the outer shaft having a proximal end having a proximal rim at the most proximal portion of the proximal end, the outer shaft comprising: a hollow outer shaft body, wherein the outer shaft body is configured to accommodate the inner shaft body therewithin; an outer face; an outer shaft opening at the outer face of the outer shaft; and iii) a ramp comprising a height that is substantially equal to a distance of a linear displacement of the inner shaft relative to the outer shaft when the inner shaft is rotated relative to the outer shaft;

wherein a longitudinal axis extends from the proximal end of the outer shaft and either the ramp extends from the proximal rim of the outer shaft in a proximal direction that is parallel to the longitudinal axis or the ramp extends from the knob in a distal direction that is parallel to the longitudinal axis when the outer shaft holds the inner shaft body therein; and wherein the inner shaft tip is configured to fit through a main slot of an implant body and rotate in a chamber of the implant body so as to lock the implant body to the inner shaft.

19. The device of claim 18, wherein the inner shaft comprises at least one material selected from carbon fiber-reinforced polymer, carbon fiber-reinforced plastic, carbon fiber-reinforced thermoplastic, glass fiber-reinforced polymer, glass fiber-reinforced plastic, and polyarylamide.

20. The device of claim 18, wherein the inner shaft body is flexible so as to fit in a curved outer shaft body.

21. The device of claim 18, wherein the inner shaft tip is substantially rectangular cuboid or cylindrically elliptical.

22. The device of claim 18, wherein the first interface comprises a cam feature.

23. The device of claim 18, wherein the outer shaft body is curved.

24. The device of claim 18, wherein the outer shaft comprises at least one material selected from the list consisting of carbon fiber-reinforced polymer, carbon fiber-reinforced plastic, carbon fiber-reinforced thermoplastic, glass fiber-reinforced polymer, glass fiber-reinforced plastic, and polyarylamide.

25. The device of claim 18, wherein either the inner or the outer shaft is injection moldable.

* * * * *